US010731195B2

(12) United States Patent
te Poele et al.

(10) Patent No.: US 10,731,195 B2
(45) Date of Patent: Aug. 4, 2020

(54) METHODS FOR THE ENZYMATIC MODIFICATION OF STEVIOL GLYCOSIDES, MODIFIED STEVIOL GLYCOSIDES OBTAINABLE THEREBY, AND THE USE THEREOF AS SWEETENERS

(71) Applicant: Rijksuniversiteit Groningen, Groningen (NL)

(72) Inventors: Evelien Maria te Poele, Groningen (NL); Lubbert Dijkhuizen, Groningen (NL); Gerrit Johannes Gerwig, Groningen (NL); Johannis Paulus Kamerling, Groningen (NL)

(73) Assignee: Rijksuniversiteit Groningen, Groningen (NL)

( * ) Notice: Subject to any disclaimer, the term of this patent is extended or adjusted under 35 U.S.C. 154(b) by 0 days.

(21) Appl. No.: 15/556,846

(22) PCT Filed: Mar. 10, 2016

(86) PCT No.: PCT/NL2016/050172
§ 371 (c)(1),
(2) Date: Sep. 8, 2017

(87) PCT Pub. No.: WO2016/144175
PCT Pub. Date: Sep. 15, 2016

(65) Prior Publication Data
US 2018/0044708 A1    Feb. 15, 2018

(30) Foreign Application Priority Data
Mar. 10, 2015   (EP) .................................... 15158421

(51) Int. Cl.
*C12P 19/56*    (2006.01)
*A23L 27/00*    (2016.01)
*A23L 27/30*    (2016.01)
*C07H 15/24*    (2006.01)
*A23L 2/60*     (2006.01)
*C07H 1/00*     (2006.01)

(52) U.S. Cl.
CPC ................. *C12P 19/56* (2013.01); *A23L 2/60* (2013.01); *A23L 27/36* (2016.08); *A23L 27/86* (2016.08); *C07H 1/00* (2013.01); *C07H 15/24* (2013.01); *A23V 2002/00* (2013.01); *A23Y 2220/71* (2013.01)

(58) Field of Classification Search
None
See application file for complete search history.

(56) References Cited

U.S. PATENT DOCUMENTS

2012/0214751 A1  8/2012  Markosyan
2013/0316043 A1  11/2013 Purkayastha
2015/0031868 A1  1/2015  Lehmann et al.

FOREIGN PATENT DOCUMENTS

WO    2013/019050 A2    2/2013

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Accession AY697430.1. Nov. 13, 2004 (Year: 2004).*
Currin et al. Chem Soc Rev. Mar. 7, 2015;44(5):1172-239. (Year: 2015).*
Van Leeuwen et al. Carbohydrate Research 343 (2008) 1237-1250 (Year: 2008).*
Te Poele, E. et al., Glucosylation of stevia using glucansucrase enzymes of Lactobacillus reuteri, 4th International Conference on Novel Enzymes; Oct. 14-17, 2014, Gent, Belgium Conference paper (Title), 2014, p. 2.
Pijning, T. et al, Flexibility of truncated and full-length glucansucrase GTF180 enzymes from Lactobacillus reuteri 180, The FEBS Journal, 2014, vol. 281, pp. 2159-2171.
Meng, X. et al., Truncation of domain V of the multidomain glucansucrase GTF180 of Lactobacillus reuteri 180 heavily impairs its polysaccharide-synthesizing ability, Applied Microbiology and Biotechnology, Jan. 15, 2015 pp. 1-10.
Ye, F. et al, Modification of stevioside using transglucosylation activity of Bacillus amyloliquefaciens ?-amylase to reduce its bitter aftertaste, LWT—Food Science and Technology, 2013, vol. 51, pp. 524-530.
Ye, F. et al., Modification of steviol glycosides using ?-amylase, LWT—Food Science and Technology, 2014, vol. 57, pp. 400-405.
Musa, A. et al., Effect of shaking velocity on mono-glycosyl-stevioside productivity via alternansucrase acceptor reaction, Journal of Molecular Catalysis B: Enzymatic, 2015, vol. 116, pp. 106-112.
Prakash, I. et al, Bioconversion of Rebaudioside I from Rebaudioside A, Molecules, 2014, vol. 19, pp. 17345-17355.
Musa, A. et al, Biotransformation of stevioside by Leuconostoc citreum SK24.002 alternansucrase acceptor reaction, Food Chemistry, 2014, vol. 146, pp. 23-29.
Venkata Sai Prakash Chaturvedula et al., Controlled hydrolysis studies of the diterpene glycosides rebaudioside D, andrebaudioside E of Stevia rebaudiana Bertoni, Journal of Chemical and Pharmaceutical Research, 2015, vol. 7, No. 3, pp. 56-62.
te Poele, E. et al, Efficient Enzymatic Transglycosylation of Rebaudioside A Using GTF180-deltaN (Mutant) enzymes of Lactobacillus Reuteri 180 Yields a Rebaudioside A Glucoside With Improved Taste, 7th World Congress on Stevia; Jun. 11-12, 2016, Berlin, Germany Abstract, Jun. 2015 (Jun. 2015), p. 1.

(Continued)

Primary Examiner — Christian L Fronda
(74) Attorney, Agent, or Firm — Banner & Witcoff, Ltd.

(57) ABSTRACT

The present invention relates generally to the production of steviol glycosides. Provided is a method for enzymatically providing a modified steviol glycoside, comprising incubating a steviol glycoside substrate in the presence of sucrose and the glucansucrase GTF180 of *Lactobacillus reuteri* strain 180, or a mutant thereof having the desired transglycosylation activity. Also provided are modified steviol glycosides obtainable by a method of the invention, and the use thereof as low-glycemic sweetener.

Figure 1:
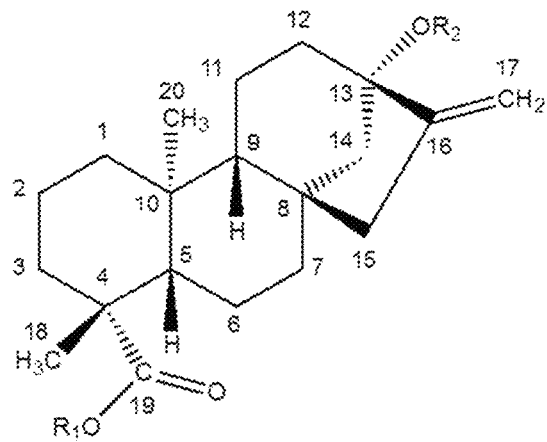

10 Claims, 12 Drawing Sheets
Specification includes a Sequence Listing.

(56) References Cited

OTHER PUBLICATIONS

Meng, X. et al., Synthesis of New Hyperbranched ?-Glucans from Sucrose by Lactobacillus reuteri 180 Glucansucrase Mutants, Journal of Agricultural and Food Chemistry, Dec. 19, 2015, vol. 64, pp. 433-442.

Meng, X. et al., Characterization of the Functional Roles of Amino Acid Residues in Acceptor-binding Subsite +1 in the Active Site of the Glucansucrase GTF180 from Lactobacillus reuteri 180, The Journal of Biological Chemistry, Dec. 11, 2015, vol. 290, pp. 30131-30141.

Prakash et al.,"Structures of Some Novel ?-Glucosyl Diterpene Glycosides from the Glycosylation of Steviol Glycosides," Molecules 2014, 19(12) pp. 20280-20294.

* cited by examiner steviol
$R_1 = R_2 = H$

| Glycoside | $R_1$ (C-19) | $R_2$ (C-13) |
|---|---|---|
| (1) Stevioside | Glc$p$(β1- [Glc1] | Glc$p$(β1-2)Glc$p$(β1- (sophorose) [Glc3]   [Glc2] |
| (2) Rebaudioside A | Glc$p$(β1- [Glc1] | Glc$p$(β1-2)[Glc$p$(β1-3)]Glc$p$(β1- [Glc3]   [Glc4]   [Glc2] |
| (3) Rebaudioside B | H- | Glc$p$(β1-2)[Glc$p$(β1-3)]Glc$p$(β1- [Glc3]   [Glc4]   [Glc2] |
| (4) Steviolbioside | H- | Glc$p$(β1-2)Glc$p$(β1- [Glc3]   [Glc2] |

FIG. 5A A
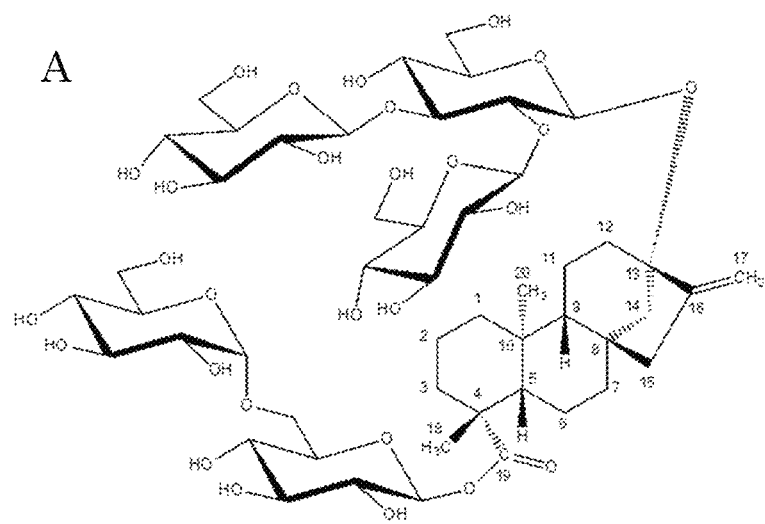
FIG. 5B B
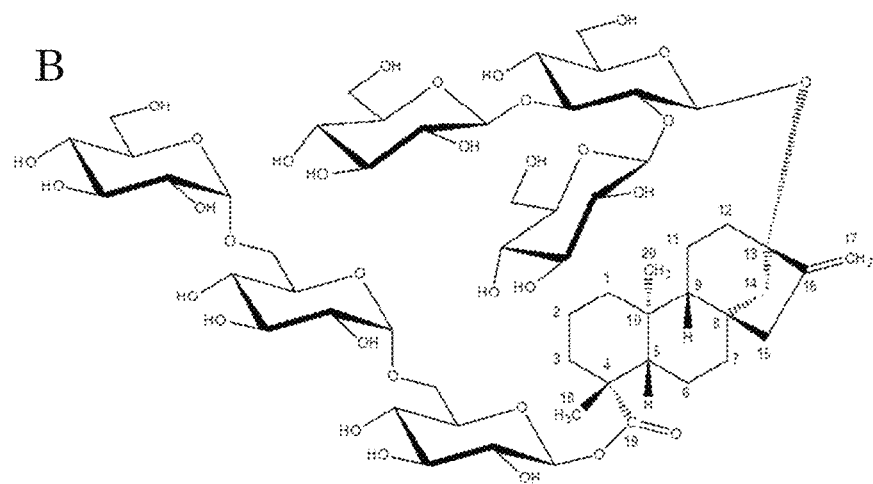
FIG. 5C C
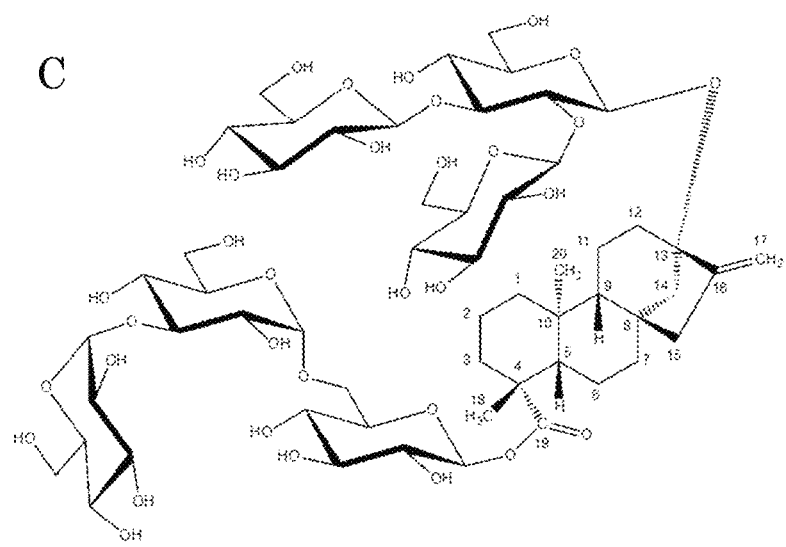

FIG. 9A

>glucansucrase GTF180 full length protein [Lactobacillus reuteri 180]

```
   1 meikkhfkly ksgkqwvtaa vatvavstal lyggvahadq qvqssttqeq tstvnadttk
  61 tvnldtntdq paqttdknqv andtttnqsk tdststtvkn ptfipvstls ssdnekqsqn
 121 ynkpdngnyg nvdaayfnnn qlhisgwhat nasqgtdsrq vivrdittkt elgrtnvtnn
 181 vlrpdvknvh nvynadnsgf dvninidfsk mkdyrdsiei vsrysgngks vdwwsqpitf
 241 dknnyayldt fevkngelha tgwnatnkai nynhhfvilf drtngkevtr qevrdgqsrp
 301 dvakvypqvv gannsgfdvt fnigdldyth qyqilsrysn adngegdyvt ywfapqsiap
 361 anqsnqgyld sfdiskngev tvtgwnatdl selqtnhyvi lfdqtagqqv asakvdlisr
 421 pdvakayptv ktaetsgfkv tfkvsnlqpg hqysvvsrfs adengngndk rhtdywyspv
 481 tlnqtasnid titmtsnglh itqwmasdns ineatpyaii lnngrevtrq kltliarpdv
 541 aavypslyns avsgfdttik ltnaqyqaln gqlqvllrfs kavdgnpngt ntvtdqfskn
 601 yattggnfdy vkvngnqief sgwhatnqsn dknsqwiivl vngkevkrql vndtkdgaag
 661 fnrndvykvn paiensimsg fqgiitlpvt vkdenvqlvh rfsndaktge qnyvdfwsev
 721 msvkdsfqkg ngplnqfglq tingqqyyid pttgqprknf llqngndwiy fdkdtgagtn
 781 alklqfdkgt isadeqyrrg neaysyddks ienvngylta dtwyrpkqil kdgttwtdsk
 841 etdmrpilmv wwpntvtqay ylnymkqygn llpaslpsfs tdadsaelnh yselvqqnie
 901 krisetgstd wlrtlmhefv tknsmwnkds envdygglql qggflkyvns dltkyansdw
 961 rlmnrtatni dgknyggaef llandidnsn pvvqaeelnw lyylmnfgti tgnnpeanfd
1021 girvdavdnv dvdllsiard yfnaaynmeq sdasankhin iledwgwddp ayvnkignpq
1081 ltmddrlrna imdtlsgapd knqalnklit qslvnrandn tenavipsyn fvrahdsnaq
1141 dqirqaiqaa tgkpygefnl ddekkgmeay indqnstnkk wnlynmpsay tiiltnkdsv
1201 prvyygdlyq dggqymehkt ryfdtitnll ktrvkyvagg qtmsvdkngi ltnvrfgkga
1261 mnatdtgtde trtegigvvi snntnlklnd gesvvlhmga ahknqkyrav ilttedgvkn
1321 ytndtdapva ytdangdlhf tntnldgqqy tavrgyanpd vtgylavwvp agaaddqdar
1381 tapsdeahtt ktayrsnaal dsnviyegfs nfiywpttes ertnvriaqn adlfkswgit
1441 tfelapqyns skdgtfldsi idngyaftdr ydlgmstpnk ygsdedlrna lqalhkaglq
1501 aiadwvpdqi ynlpgkeavt vtrsddhgtt wevspiknvv yitntiggge yqkkyggefl
1561 dtlqkeypql fsqvypvtqt tidpsvkike wsakyfngtn ilhrgagyvl rsndgkyynl
1621 gtstqqflps qlsvqdnegy gfvkegnnyh yydenkqmvk dafiqdsvgn wyyfdkngnm
1681 vanqspveis sngasqtylf lnngtsfrsg lvktdagtyy ydgdgrmvrn qtvsdgamty
1741 vldengklvs esfdssatea hplkpgdlng qk
//
```

(SEQ ID NO:1)

FIG. 9B

>N-terminally truncated glucansucrase GTF180-ΔN [Lactobacillus reuteri 180]
```
    1 mgingqqyyi dpttgqprkn fllqngndwi yfdkdtgagt nalklqfdkg tisadeqyrr
   61 gneaysyddk sienvngylt adtwyrpkqi lkdgttwtds ketdmrpilm vwwpntvtqa
  121 yylnymkqyg nllpaslpsf stdadsaeln hyselvqqni ekrisetgst dwlrtlmhef
  181 vtknsmwnkd senvdygglq lqggflkyvn sdltkyansd wrlmnrtatn idgknyggae
  241 fllandidns npvvqaeeln wlyylmnfgt itgnnpeanf dgirvdavdn vdvdllsiar
  301 dyfnaaynme qsdasankhi niledwgwdd payvnkignp qltmddrlrn aimdtlsgap
  361 dknqalnkli tqslvnrand ntenavipsy nfvrahdsna qdqirqaiqa atgkpygefn
  421 lddekkgmea yindqnstnk kwnlynmpsa ytilltnkds vprvyygdly qdgqymehk
  481 tryfdtitnl lktrvkyvaq gqtmsvdkng iltnvrfgkg amnatdtgtd etrtegigvv
  541 isnntnlkln dgesvvlhmg aahkmqkyra vilttedgvk nytndtdapv aytdangdlh
  601 ftntnldgqq ytavrgyanp dvtgylavwv pagaaddqda rtapsdeaht tktayrsnaa
  661 ldsnviyegf snfiywptte sertnvriaq nadlfkswgi ttfelapqyn sskdgtflds
  721 iidngyaftd rydlgmstpn kygsdedlrn alqalhkagl qaiadwvpdq iynlpgkeav
  781 tvtrsddhgt twevspiknv vyitntiggq eyqkkyggef ldtlqkeypq lfsqvypvtq
  841 ttidpsvkik ewsakyfngt nilhrgagyv lrsndgkyyn lgtstqqflp sqlsvqdneg
  901 ygfvkegnny hyydenkqmv kdafiqdsvg nwyyldkngn mvanqspvei ssngasgtyl
  961 flnngtsfrs glvktdagty yydgdgrmvr nqtvsdgamt yvldengklv sesfdssate
 1021 ahplkpgdln gqk
//
```

(SEQ ID NO:2)

FIG. 9C

>N-terminally truncated and domain V truncated glucansucrase GTF180-ΔNΔV
[Lactobacillus reuteri 180]

```
  1  mdeqyrrgne aysyddksie nvngyltadt wyrpkqilkd gttwtdsket dmrpilmvww
 61  pntvtqayyl nymkqygnll paslpsfstd adsaelnhys elvqqniekr isetgstdwl
121  rtlmhefvtk nsmwnkdsen vdygglqlqg gflkyvnsdl tkyansdwrl mnrtatnidg
181  knyggaefll andidnsnpv vqaeelnwly ylmnfgtitg nnpeanfdgi rvdavdnvdv
241  dllsiardyf naaynmeqsd asankhinil edwgwddpay vnkignpqlt mddrlrnaim
301  dtlsgapdkn qalnklitqs lvnrandnte navipsynfv rahdsnaqdq irqaiqaatg
361  kpygefnldd ekkgmeayin dqnstnkkwn lynmpsayti lltnkdsvpr vyygdlyqdg
421  gqymehktry fdtitnllkt rvkyvaggqt msvdkngilt nvrfgkgamn atdtgtdetr
481  tegigvvisn ntnlklndge svvihmgaah knqkyravil ttedgvknyt ndtdapvayt
541  dangdlhftn tnldgqqyta vrgyanpdvt gylavwvpag aaddqdarta psdeahttkt
601  ayrsnaalds nviyegfsnf iywptteser tnvriaqnad lfkswgittf elapqynssk
661  dgtfldsiid ngyaftdryd lgmstpnkyg sdedlrnaiq alhkaglqai adwvpdqiyn
721  lpgkeavtvt rsddhgttwe vspiknvvyi tntigggeyq kkyggefldt lqkeypqlfs
781  qvypvtqtti dpsvkikews akyfngtnil hrgagyvlrs ndgkyynlgt stqqflpsql
841  svqd
//
```

(SEQ ID NO:3)

SEQUENCE LISTING

```
<160> NUMBER OF SEQ ID NOS: 3

<210> SEQ ID NO 1
<211> LENGTH: 1772
<212> TYPE: PRT
<213> ORGANISM: Lactobacillus reuteri

<400> SEQUENCE: 1

Met Glu Ile Lys Lys His Phe Lys Leu Tyr Lys Ser Gly Lys Gln Trp
1               5                   10                  15
```

-continued

```
Val Thr Ala Ala Val Ala Thr Val Ala Val Ser Thr Ala Leu Leu Tyr
            20                  25                  30

Gly Gly Val Ala His Ala Asp Gln Gln Val Gln Ser Ser Thr Thr Gln
        35                  40                  45

Glu Gln Thr Ser Thr Val Asn Ala Asp Thr Thr Lys Thr Val Asn Leu
    50                  55                  60

Asp Thr Asn Thr Asp Gln Pro Ala Gln Thr Thr Asp Lys Asn Gln Val
65                  70                  75                  80

Ala Asn Asp Thr Thr Thr Asn Gln Ser Lys Thr Asp Ser Thr Ser Thr
                85                  90                  95

Thr Val Lys Asn Pro Thr Phe Ile Pro Val Ser Thr Leu Ser Ser Ser
            100                 105                 110

Asp Asn Glu Lys Gln Ser Gln Asn Tyr Asn Lys Pro Asp Asn Gly Asn
        115                 120                 125

Tyr Gly Asn Val Asp Ala Ala Tyr Phe Asn Asn Gln Leu His Ile
    130                 135                 140

Ser Gly Trp His Ala Thr Asn Ala Ser Gln Gly Thr Asp Ser Arg Gln
145                 150                 155                 160

Val Ile Val Arg Asp Ile Thr Thr Lys Thr Glu Leu Gly Arg Thr Asn
                165                 170                 175

Val Thr Asn Asn Val Leu Arg Pro Asp Val Lys Asn Val His Asn Val
            180                 185                 190

Tyr Asn Ala Asp Asn Ser Gly Phe Asp Val Asn Ile Asn Ile Asp Phe
        195                 200                 205

Ser Lys Met Lys Asp Tyr Arg Asp Ser Ile Glu Ile Val Ser Arg Tyr
    210                 215                 220

Ser Gly Asn Gly Lys Ser Val Asp Trp Trp Ser Gln Pro Ile Thr Phe
225                 230                 235                 240

Asp Lys Asn Asn Tyr Ala Tyr Leu Asp Thr Phe Glu Val Lys Asn Gly
                245                 250                 255

Glu Leu His Ala Thr Gly Trp Asn Ala Thr Asn Lys Ala Ile Asn Tyr
            260                 265                 270

Asn His His Phe Val Ile Leu Phe Asp Arg Thr Asn Gly Lys Glu Val
        275                 280                 285

Thr Arg Gln Glu Val Arg Asp Gly Gln Ser Arg Pro Asp Val Ala Lys
    290                 295                 300

Val Tyr Pro Gln Val Val Gly Ala Asn Asn Ser Gly Phe Asp Val Thr
305                 310                 315                 320

Phe Asn Ile Gly Asp Leu Asp Tyr Thr His Gln Tyr Gln Ile Leu Ser
                325                 330                 335

Arg Tyr Ser Asn Ala Asp Asn Gly Glu Gly Asp Tyr Val Thr Tyr Trp
            340                 345                 350

Phe Ala Pro Gln Ser Ile Ala Pro Ala Asn Gln Ser Asn Gln Gly Tyr
        355                 360                 365

Leu Asp Ser Phe Asp Ile Ser Lys Asn Gly Glu Val Thr Val Thr Gly
    370                 375                 380

Trp Asn Ala Thr Asp Leu Ser Glu Leu Gln Thr Asn His Tyr Val Ile
385                 390                 395                 400

Leu Phe Asp Gln Thr Ala Gly Gln Gln Val Ala Ser Ala Lys Val Asp
                405                 410                 415

Leu Ile Ser Arg Pro Asp Val Ala Lys Ala Tyr Pro Thr Val Lys Thr
            420                 425                 430

Ala Glu Thr Ser Gly Phe Lys Val Thr Phe Lys Val Ser Asn Leu Gln
```

```
                    435                 440                 445
Pro Gly His Gln Tyr Ser Val Val Ser Arg Phe Ser Ala Asp Glu Asn
450                 455                 460

Gly Asn Gly Asn Asp Lys Arg His Thr Asp Tyr Trp Tyr Ser Pro Val
465                 470                 475                 480

Thr Leu Asn Gln Thr Ala Ser Asn Ile Asp Thr Ile Thr Met Thr Ser
                    485                 490                 495

Asn Gly Leu His Ile Thr Gly Trp Met Ala Ser Asp Asn Ser Ile Asn
                500                 505                 510

Glu Ala Thr Pro Tyr Ala Ile Ile Leu Asn Asn Gly Arg Glu Val Thr
            515                 520                 525

Arg Gln Lys Leu Thr Leu Ile Ala Arg Pro Asp Val Ala Ala Val Tyr
        530                 535                 540

Pro Ser Leu Tyr Asn Ser Ala Val Ser Gly Phe Asp Thr Thr Ile Lys
545                 550                 555                 560

Leu Thr Asn Ala Gln Tyr Gln Ala Leu Asn Gly Gln Leu Gln Val Leu
                    565                 570                 575

Leu Arg Phe Ser Lys Ala Val Asp Gly Asn Pro Asn Gly Thr Asn Thr
                580                 585                 590

Val Thr Asp Gln Phe Ser Lys Asn Tyr Ala Thr Thr Gly Gly Asn Phe
            595                 600                 605

Asp Tyr Val Lys Val Asn Gly Asn Gln Ile Glu Phe Ser Gly Trp His
        610                 615                 620

Ala Thr Asn Gln Ser Asn Asp Lys Asn Ser Gln Trp Ile Ile Val Leu
625                 630                 635                 640

Val Asn Gly Lys Glu Val Lys Arg Gln Leu Val Asn Asp Thr Lys Asp
                    645                 650                 655

Gly Ala Ala Gly Phe Asn Arg Asn Asp Val Tyr Lys Val Asn Pro Ala
                660                 665                 670

Ile Glu Asn Ser Ile Met Ser Gly Phe Gln Gly Ile Ile Thr Leu Pro
            675                 680                 685

Val Thr Val Lys Asp Glu Asn Val Gln Leu Val His Arg Phe Ser Asn
        690                 695                 700

Asp Ala Lys Thr Gly Glu Gly Asn Tyr Val Asp Phe Trp Ser Glu Val
705                 710                 715                 720

Met Ser Val Lys Asp Ser Phe Gln Lys Gly Asn Gly Pro Leu Asn Gln
                    725                 730                 735

Phe Gly Leu Gln Thr Ile Asn Gly Gln Gln Tyr Tyr Ile Asp Pro Thr
                740                 745                 750

Thr Gly Gln Pro Arg Lys Asn Phe Leu Leu Gln Asn Gly Asn Asp Trp
            755                 760                 765

Ile Tyr Phe Asp Lys Asp Thr Gly Ala Gly Thr Asn Ala Leu Lys Leu
        770                 775                 780

Gln Phe Asp Lys Gly Thr Ile Ser Ala Asp Glu Gln Tyr Arg Arg Gly
785                 790                 795                 800

Asn Glu Ala Tyr Ser Tyr Asp Asp Lys Ser Ile Glu Asn Val Asn Gly
                    805                 810                 815

Tyr Leu Thr Ala Asp Thr Trp Tyr Arg Pro Lys Gln Ile Leu Lys Asp
                820                 825                 830

Gly Thr Thr Trp Thr Asp Ser Lys Glu Thr Asp Met Arg Pro Ile Leu
            835                 840                 845

Met Val Trp Trp Pro Asn Thr Val Thr Gln Ala Tyr Tyr Leu Asn Tyr
        850                 855                 860
```

```
Met Lys Gln Tyr Gly Asn Leu Leu Pro Ala Ser Leu Pro Ser Phe Ser
865                 870                 875                 880

Thr Asp Ala Asp Ser Ala Glu Leu Asn His Tyr Ser Glu Leu Val Gln
                885                 890                 895

Gln Asn Ile Glu Lys Arg Ile Ser Glu Thr Gly Ser Thr Asp Trp Leu
            900                 905                 910

Arg Thr Leu Met His Glu Phe Val Thr Lys Asn Ser Met Trp Asn Lys
        915                 920                 925

Asp Ser Glu Asn Val Asp Tyr Gly Gly Leu Gln Leu Gln Gly Gly Phe
    930                 935                 940

Leu Lys Tyr Val Asn Ser Asp Leu Thr Lys Tyr Ala Asn Ser Asp Trp
945                 950                 955                 960

Arg Leu Met Asn Arg Thr Ala Thr Asn Ile Asp Gly Lys Asn Tyr Gly
                965                 970                 975

Gly Ala Glu Phe Leu Leu Ala Asn Asp Ile Asp Asn Ser Asn Pro Val
            980                 985                 990

Val Gln Ala Glu Glu Leu Asn Trp Leu Tyr Tyr Leu Met Asn Phe Gly
        995                 1000                1005

Thr Ile Thr Gly Asn Asn Pro Glu Ala Asn Phe Asp Gly Ile Arg
    1010                1015                1020

Val Asp Ala Val Asp Asn Val Asp Val Asp Leu Leu Ser Ile Ala
    1025                1030                1035

Arg Asp Tyr Phe Asn Ala Ala Tyr Asn Met Glu Gln Ser Asp Ala
    1040                1045                1050

Ser Ala Asn Lys His Ile Asn Ile Leu Glu Asp Trp Gly Trp Asp
    1055                1060                1065

Asp Pro Ala Tyr Val Asn Lys Ile Gly Asn Pro Gln Leu Thr Met
    1070                1075                1080

Asp Asp Arg Leu Arg Asn Ala Ile Met Asp Thr Leu Ser Gly Ala
    1085                1090                1095

Pro Asp Lys Asn Gln Ala Leu Asn Lys Leu Ile Thr Gln Ser Leu
    1100                1105                1110

Val Asn Arg Ala Asn Asp Asn Thr Glu Asn Ala Val Ile Pro Ser
    1115                1120                1125

Tyr Asn Phe Val Arg Ala His Asp Ser Asn Ala Gln Asp Gln Ile
    1130                1135                1140

Arg Gln Ala Ile Gln Ala Ala Thr Gly Lys Pro Tyr Gly Glu Phe
    1145                1150                1155

Asn Leu Asp Asp Glu Lys Lys Gly Met Glu Ala Tyr Ile Asn Asp
    1160                1165                1170

Gln Asn Ser Thr Asn Lys Lys Trp Asn Leu Tyr Asn Met Pro Ser
    1175                1180                1185

Ala Tyr Thr Ile Leu Leu Thr Asn Lys Asp Ser Val Pro Arg Val
    1190                1195                1200

Tyr Tyr Gly Asp Leu Tyr Gln Asp Gly Gly Gln Tyr Met Glu His
    1205                1210                1215

Lys Thr Arg Tyr Phe Asp Thr Ile Thr Asn Leu Leu Lys Thr Arg
    1220                1225                1230

Val Lys Tyr Val Ala Gly Gly Gln Thr Met Ser Val Asp Lys Asn
    1235                1240                1245

Gly Ile Leu Thr Asn Val Arg Phe Gly Lys Gly Ala Met Asn Ala
    1250                1255                1260
```

```
Thr Asp Thr Gly Thr Asp Glu Thr Arg Thr Glu Gly Ile Gly Val
1265                1270                1275

Val Ile Ser Asn Asn Thr Asn Leu Lys Leu Asn Asp Gly Glu Ser
1280                1285                1290

Val Val Leu His Met Gly Ala His Lys Asn Gln Lys Tyr Arg
1295                1300                1305

Ala Val Ile Leu Thr Thr Glu Asp Gly Val Lys Asn Tyr Thr Asn
1310                1315                1320

Asp Thr Asp Ala Pro Val Ala Tyr Thr Asp Ala Asn Gly Asp Leu
1325                1330                1335

His Phe Thr Asn Thr Asn Leu Asp Gly Gln Gln Tyr Thr Ala Val
1340                1345                1350

Arg Gly Tyr Ala Asn Pro Asp Val Thr Gly Tyr Leu Ala Val Trp
1355                1360                1365

Val Pro Ala Gly Ala Ala Asp Asp Gln Asp Ala Arg Thr Ala Pro
1370                1375                1380

Ser Asp Glu Ala His Thr Thr Lys Thr Ala Tyr Arg Ser Asn Ala
1385                1390                1395

Ala Leu Asp Ser Asn Val Ile Tyr Glu Gly Phe Ser Asn Phe Ile
1400                1405                1410

Tyr Trp Pro Thr Thr Glu Ser Glu Arg Thr Asn Val Arg Ile Ala
1415                1420                1425

Gln Asn Ala Asp Leu Phe Lys Ser Trp Gly Ile Thr Thr Phe Glu
1430                1435                1440

Leu Ala Pro Gln Tyr Asn Ser Ser Lys Asp Gly Thr Phe Leu Asp
1445                1450                1455

Ser Ile Ile Asp Asn Gly Tyr Ala Phe Thr Asp Arg Tyr Asp Leu
1460                1465                1470

Gly Met Ser Thr Pro Asn Lys Tyr Gly Ser Asp Glu Asp Leu Arg
1475                1480                1485

Asn Ala Leu Gln Ala Leu His Lys Ala Gly Leu Gln Ala Ile Ala
1490                1495                1500

Asp Trp Val Pro Asp Gln Ile Tyr Asn Leu Pro Gly Lys Glu Ala
1505                1510                1515

Val Thr Val Thr Arg Ser Asp Asp His Gly Thr Thr Trp Glu Val
1520                1525                1530

Ser Pro Ile Lys Asn Val Val Tyr Ile Thr Asn Thr Ile Gly Gly
1535                1540                1545

Gly Glu Tyr Gln Lys Lys Tyr Gly Gly Glu Phe Leu Asp Thr Leu
1550                1555                1560

Gln Lys Glu Tyr Pro Gln Leu Phe Ser Gln Val Tyr Pro Val Thr
1565                1570                1575

Gln Thr Thr Ile Asp Pro Ser Val Lys Ile Lys Glu Trp Ser Ala
1580                1585                1590

Lys Tyr Phe Asn Gly Thr Asn Ile Leu His Arg Gly Ala Gly Tyr
1595                1600                1605

Val Leu Arg Ser Asn Asp Gly Lys Tyr Tyr Asn Leu Gly Thr Ser
1610                1615                1620

Thr Gln Gln Phe Leu Pro Ser Gln Leu Ser Val Gln Asp Asn Glu
1625                1630                1635

Gly Tyr Gly Phe Val Lys Glu Gly Asn Asn Tyr His Tyr Tyr Asp
1640                1645                1650

Glu Asn Lys Gln Met Val Lys Asp Ala Phe Ile Gln Asp Ser Val
```

```
                1655                1660                1665

Gly Asn Trp Tyr Tyr Phe Asp Lys Asn Gly Asn Met Val Ala Asn
        1670                1675                1680

Gln Ser Pro Val Glu Ile Ser Ser Asn Gly Ala Ser Gly Thr Tyr
        1685                1690                1695

Leu Phe Leu Asn Asn Gly Thr Ser Phe Arg Ser Gly Leu Val Lys
        1700                1705                1710

Thr Asp Ala Gly Thr Tyr Tyr Asp Gly Asp Gly Arg Met Val
        1715                1720                1725

Arg Asn Gln Thr Val Ser Asp Gly Ala Met Thr Tyr Val Leu Asp
        1730                1735                1740

Glu Asn Gly Lys Leu Val Ser Glu Ser Phe Asp Ser Ser Ala Thr
        1745                1750                1755

Glu Ala His Pro Leu Lys Pro Gly Asp Leu Asn Gly Gln Lys
        1760                1765                1770

<210> SEQ ID NO 2
<211> LENGTH: 1033
<212> TYPE: PRT
<213> ORGANISM: Lactobacillus reuteri

<400> SEQUENCE: 2

Met Gly Ile Asn Gly Gln Gln Tyr Tyr Ile Asp Pro Thr Thr Gly Gln
1               5                   10                  15

Pro Arg Lys Asn Phe Leu Leu Gln Asn Gly Asn Asp Trp Ile Tyr Phe
                20                  25                  30

Asp Lys Asp Thr Gly Ala Gly Thr Asn Ala Leu Lys Leu Gln Phe Asp
            35                  40                  45

Lys Gly Thr Ile Ser Ala Asp Glu Gln Tyr Arg Arg Gly Asn Glu Ala
        50                  55                  60

Tyr Ser Tyr Asp Asp Lys Ser Ile Glu Asn Val Asn Gly Tyr Leu Thr
65                  70                  75                  80

Ala Asp Thr Trp Tyr Arg Pro Lys Gln Ile Leu Lys Asp Gly Thr Thr
                85                  90                  95

Trp Thr Asp Ser Lys Glu Thr Asp Met Arg Pro Ile Leu Met Val Trp
            100                 105                 110

Trp Pro Asn Thr Val Thr Gln Ala Tyr Tyr Leu Asn Tyr Met Lys Gln
        115                 120                 125

Tyr Gly Asn Leu Leu Pro Ala Ser Leu Pro Ser Phe Ser Thr Asp Ala
    130                 135                 140

Asp Ser Ala Glu Leu Asn His Tyr Ser Glu Leu Val Gln Gln Asn Ile
145                 150                 155                 160

Glu Lys Arg Ile Ser Glu Thr Gly Ser Thr Asp Trp Leu Arg Thr Leu
                165                 170                 175

Met His Glu Phe Val Thr Lys Asn Ser Met Trp Asn Lys Asp Ser Glu
            180                 185                 190

Asn Val Asp Tyr Gly Gly Leu Gln Leu Gln Gly Gly Phe Leu Lys Tyr
        195                 200                 205

Val Asn Ser Asp Leu Thr Lys Tyr Ala Asn Ser Asp Trp Arg Leu Met
    210                 215                 220

Asn Arg Thr Ala Thr Asn Ile Asp Gly Lys Asn Tyr Gly Gly Ala Glu
225                 230                 235                 240

Phe Leu Leu Ala Asn Asp Ile Asp Asn Ser Asn Pro Val Val Gln Ala
                245                 250                 255
```

```
Glu Glu Leu Asn Trp Leu Tyr Tyr Leu Met Asn Phe Gly Thr Ile Thr
            260                 265                 270

Gly Asn Asn Pro Glu Ala Asn Phe Asp Gly Ile Arg Val Asp Ala Val
            275                 280                 285

Asp Asn Val Asp Val Asp Leu Leu Ser Ile Ala Arg Asp Tyr Phe Asn
            290                 295                 300

Ala Ala Tyr Asn Met Glu Gln Ser Asp Ala Ser Ala Asn Lys His Ile
305                 310                 315                 320

Asn Ile Leu Glu Asp Trp Gly Trp Asp Asp Pro Ala Tyr Val Asn Lys
                325                 330                 335

Ile Gly Asn Pro Gln Leu Thr Met Asp Asp Arg Leu Arg Asn Ala Ile
            340                 345                 350

Met Asp Thr Leu Ser Gly Ala Pro Asp Lys Asn Gln Ala Leu Asn Lys
            355                 360                 365

Leu Ile Thr Gln Ser Leu Val Asn Arg Ala Asn Asp Asn Thr Glu Asn
            370                 375                 380

Ala Val Ile Pro Ser Tyr Asn Phe Val Arg Ala His Asp Ser Asn Ala
385                 390                 395                 400

Gln Asp Gln Ile Arg Gln Ala Ile Gln Ala Ala Thr Gly Lys Pro Tyr
                405                 410                 415

Gly Glu Phe Asn Leu Asp Asp Glu Lys Lys Gly Met Glu Ala Tyr Ile
            420                 425                 430

Asn Asp Gln Asn Ser Thr Asn Lys Lys Trp Asn Leu Tyr Asn Met Pro
            435                 440                 445

Ser Ala Tyr Thr Ile Leu Leu Thr Asn Lys Asp Ser Val Pro Arg Val
450                 455                 460

Tyr Tyr Gly Asp Leu Tyr Gln Asp Gly Gly Gln Tyr Met Glu His Lys
465                 470                 475                 480

Thr Arg Tyr Phe Asp Thr Ile Thr Asn Leu Leu Lys Thr Arg Val Lys
                485                 490                 495

Tyr Val Ala Gly Gly Gln Thr Met Ser Val Asp Lys Asn Gly Ile Leu
            500                 505                 510

Thr Asn Val Arg Phe Gly Lys Gly Ala Met Asn Ala Thr Asp Thr Gly
            515                 520                 525

Thr Asp Glu Thr Arg Thr Glu Gly Ile Gly Val Val Ile Ser Asn Asn
            530                 535                 540

Thr Asn Leu Lys Leu Asn Asp Gly Glu Ser Val Val Leu His Met Gly
545                 550                 555                 560

Ala Ala His Lys Asn Gln Lys Tyr Arg Ala Val Ile Leu Thr Thr Glu
                565                 570                 575

Asp Gly Val Lys Asn Tyr Thr Asn Asp Thr Asp Ala Pro Val Ala Tyr
            580                 585                 590

Thr Asp Ala Asn Gly Asp Leu His Phe Thr Asn Thr Asn Leu Asp Gly
            595                 600                 605

Gln Gln Tyr Thr Ala Val Arg Gly Tyr Ala Asn Pro Asp Val Thr Gly
            610                 615                 620

Tyr Leu Ala Val Trp Val Pro Ala Gly Ala Ala Asp Asp Gln Asp Ala
625                 630                 635                 640

Arg Thr Ala Pro Ser Asp Glu Ala His Thr Thr Lys Thr Ala Tyr Arg
                645                 650                 655

Ser Asn Ala Ala Leu Asp Ser Asn Val Ile Tyr Glu Gly Phe Ser Asn
            660                 665                 670

Phe Ile Tyr Trp Pro Thr Thr Glu Ser Glu Arg Thr Asn Val Arg Ile
```

-continued

Ala Gln Asn Ala Asp Leu Phe Lys Ser Trp Gly Ile Thr Thr Phe Glu
            675                 680                 685

Leu Ala Pro Gln Tyr Asn Ser Ser Lys Asp Gly Thr Phe Leu Asp Ser
    690                 695                 700

Ile Ile Asp Asn Gly Tyr Ala Phe Thr Asp Arg Tyr Asp Leu Gly Met
705                 710                 715                 720

Ser Thr Pro Asn Lys Tyr Gly Ser Asp Glu Asp Leu Arg Asn Ala Leu
            725                 730                 735

Gln Ala Leu His Lys Ala Gly Leu Gln Ala Ile Ala Asp Trp Val Pro
        740                 745                 750

Asp Gln Ile Tyr Asn Leu Pro Gly Lys Glu Ala Val Thr Val Thr Arg
    755                 760                 765

Ser Asp Asp His Gly Thr Thr Trp Glu Val Ser Pro Ile Lys Asn Val
770                 775                 780

Val Tyr Ile Thr Asn Thr Ile Gly Gly Gly Glu Tyr Gln Lys Lys Tyr
            785                 790                 795             800

Gly Gly Glu Phe Leu Asp Thr Leu Gln Lys Glu Tyr Pro Gln Leu Phe
        805                 810                 815

Ser Gln Val Tyr Pro Val Thr Gln Thr Thr Ile Asp Pro Ser Val Lys
    820                 825                 830

Ile Lys Glu Trp Ser Ala Lys Tyr Phe Asn Gly Thr Asn Ile Leu His
835                 840                 845

Arg Gly Ala Gly Tyr Val Leu Arg Ser Asn Asp Gly Lys Tyr Tyr Asn
850                 855                 860

Leu Gly Thr Ser Thr Gln Gln Phe Leu Pro Ser Gln Leu Ser Val Gln
865                 870                 875                 880

Asp Asn Glu Gly Tyr Gly Phe Val Lys Glu Gly Asn Asn Tyr His Tyr
            885                 890                 895

Tyr Asp Glu Asn Lys Gln Met Val Lys Asp Ala Phe Ile Gln Asp Ser
        900                 905                 910

Val Gly Asn Trp Tyr Tyr Leu Asp Lys Asn Gly Asn Met Val Ala Asn
    915                 920                 925

Gln Ser Pro Val Glu Ile Ser Ser Asn Gly Ala Ser Gly Thr Tyr Leu
930                 935                 940

Phe Leu Asn Asn Gly Thr Ser Phe Arg Ser Gly Leu Val Lys Thr Asp
            945                 950                 955             960

Ala Gly Thr Tyr Tyr Tyr Asp Gly Asp Gly Arg Met Val Arg Asn Gln
        965                 970                 975

Thr Val Ser Asp Gly Ala Met Thr Tyr Val Leu Asp Glu Asn Gly Lys
    980                 985                 990

Leu Val Ser Glu Ser Phe Asp Ser Ser Ala Thr Glu Ala His Pro
995                 1000                1005

Leu Lys Pro Gly Asp Leu Asn Gly Gln Lys
        1010                1015

<210> SEQ ID NO 3
<211> LENGTH: 844
<212> TYPE: PRT
<213> ORGANISM: Lactobacillus reuteri

<400> SEQUENCE: 3

Met Asp Glu Gln Tyr Arg Arg Gly Asn Glu Ala Tyr Ser Tyr Asp Asp
1               5                   10                  15

-continued

```
Lys Ser Ile Glu Asn Val Asn Gly Tyr Leu Thr Ala Asp Thr Trp Tyr
            20                  25                  30

Arg Pro Lys Gln Ile Leu Lys Asp Gly Thr Thr Trp Thr Asp Ser Lys
            35                  40                  45

Glu Thr Asp Met Arg Pro Ile Leu Met Val Trp Trp Pro Asn Thr Val
 50                  55                  60

Thr Gln Ala Tyr Tyr Leu Asn Tyr Met Lys Gln Tyr Gly Asn Leu Leu
 65                  70                  75                  80

Pro Ala Ser Leu Pro Ser Phe Ser Thr Asp Ala Asp Ser Ala Glu Leu
                85                  90                  95

Asn His Tyr Ser Glu Leu Val Gln Gln Asn Ile Glu Lys Arg Ile Ser
                100                 105                 110

Glu Thr Gly Ser Thr Asp Trp Leu Arg Thr Leu Met His Glu Phe Val
            115                 120                 125

Thr Lys Asn Ser Met Trp Asn Lys Asp Ser Glu Asn Val Asp Tyr Gly
        130                 135                 140

Gly Leu Gln Leu Gln Gly Gly Phe Leu Lys Tyr Val Asn Ser Asp Leu
145                 150                 155                 160

Thr Lys Tyr Ala Asn Ser Asp Trp Arg Leu Met Asn Arg Thr Ala Thr
                165                 170                 175

Asn Ile Asp Gly Lys Asn Tyr Gly Gly Ala Glu Phe Leu Leu Ala Asn
                180                 185                 190

Asp Ile Asp Asn Ser Asn Pro Val Val Gln Ala Glu Glu Leu Asn Trp
            195                 200                 205

Leu Tyr Tyr Leu Met Asn Phe Gly Thr Ile Thr Gly Asn Asn Pro Glu
210                 215                 220

Ala Asn Phe Asp Gly Ile Arg Val Asp Ala Val Asp Asn Val Asp Val
225                 230                 235                 240

Asp Leu Leu Ser Ile Ala Arg Asp Tyr Phe Asn Ala Ala Tyr Asn Met
                245                 250                 255

Glu Gln Ser Asp Ala Ser Ala Asn Lys His Ile Asn Ile Leu Glu Asp
            260                 265                 270

Trp Gly Trp Asp Asp Pro Ala Tyr Val Asn Lys Ile Gly Asn Pro Gln
        275                 280                 285

Leu Thr Met Asp Asp Arg Leu Arg Asn Ala Ile Met Asp Thr Leu Ser
    290                 295                 300

Gly Ala Pro Asp Lys Asn Gln Ala Leu Asn Lys Leu Ile Thr Gln Ser
305                 310                 315                 320

Leu Val Asn Arg Ala Asn Asp Asn Thr Glu Asn Ala Val Ile Pro Ser
                325                 330                 335

Tyr Asn Phe Val Arg Ala His Asp Ser Asn Ala Gln Asp Gln Ile Arg
                340                 345                 350

Gln Ala Ile Gln Ala Ala Thr Gly Lys Pro Tyr Gly Glu Phe Asn Leu
            355                 360                 365

Asp Asp Glu Lys Lys Gly Met Glu Ala Tyr Ile Asn Asp Gln Asn Ser
        370                 375                 380

Thr Asn Lys Lys Trp Asn Leu Tyr Asn Met Pro Ser Ala Tyr Thr Ile
385                 390                 395                 400

Leu Leu Thr Asn Lys Asp Ser Val Pro Arg Val Tyr Tyr Gly Asp Leu
                405                 410                 415

Tyr Gln Asp Gly Gly Gln Tyr Met Glu His Lys Thr Arg Tyr Phe Asp
            420                 425                 430

Thr Ile Thr Asn Leu Leu Lys Thr Arg Val Lys Tyr Val Ala Gly Gly
```

```
                435                 440                 445
Gln Thr Met Ser Val Asp Lys Asn Gly Ile Leu Thr Asn Val Arg Phe
450                 455                 460

Gly Lys Gly Ala Met Asn Ala Thr Asp Thr Gly Thr Asp Glu Thr Arg
465                 470                 475                 480

Thr Glu Gly Ile Gly Val Val Ile Ser Asn Thr Asn Leu Lys Leu
                    485                 490                 495

Asn Asp Gly Glu Ser Val Val Leu His Met Gly Ala Ala His Lys Asn
                500                 505                 510

Gln Lys Tyr Arg Ala Val Ile Leu Thr Thr Glu Asp Gly Val Lys Asn
            515                 520                 525

Tyr Thr Asn Asp Thr Asp Ala Pro Val Ala Tyr Thr Asp Ala Asn Gly
        530                 535                 540

Asp Leu His Phe Thr Asn Thr Asn Leu Asp Gly Gln Gln Tyr Thr Ala
545                 550                 555                 560

Val Arg Gly Tyr Ala Asn Pro Asp Val Thr Gly Tyr Leu Ala Val Trp
                565                 570                 575

Val Pro Ala Gly Ala Ala Asp Asp Gln Asp Ala Arg Thr Ala Pro Ser
                580                 585                 590

Asp Glu Ala His Thr Thr Lys Thr Ala Tyr Arg Ser Asn Ala Ala Leu
            595                 600                 605

Asp Ser Asn Val Ile Tyr Glu Gly Phe Ser Asn Phe Ile Tyr Trp Pro
        610                 615                 620

Thr Thr Glu Ser Glu Arg Thr Asn Val Arg Ile Ala Gln Asn Ala Asp
625                 630                 635                 640

Leu Phe Lys Ser Trp Gly Ile Thr Thr Phe Glu Leu Ala Pro Gln Tyr
                645                 650                 655

Asn Ser Ser Lys Asp Gly Thr Phe Leu Asp Ser Ile Ile Asp Asn Gly
                660                 665                 670

Tyr Ala Phe Thr Asp Arg Tyr Asp Leu Gly Met Ser Thr Pro Asn Lys
            675                 680                 685

Tyr Gly Ser Asp Glu Asp Leu Arg Asn Ala Leu Gln Ala Leu His Lys
        690                 695                 700

Ala Gly Leu Gln Ala Ile Ala Asp Trp Val Pro Asp Gln Ile Tyr Asn
705                 710                 715                 720

Leu Pro Gly Lys Glu Ala Val Thr Val Thr Arg Ser Asp Asp His Gly
                725                 730                 735

Thr Thr Trp Glu Val Ser Pro Ile Lys Asn Val Val Tyr Ile Thr Asn
                740                 745                 750

Thr Ile Gly Gly Gly Glu Tyr Gln Lys Lys Tyr Gly Gly Glu Phe Leu
            755                 760                 765

Asp Thr Leu Gln Lys Glu Tyr Pro Gln Leu Phe Ser Gln Val Tyr Pro
        770                 775                 780

Val Thr Gln Thr Thr Ile Asp Pro Ser Val Lys Ile Lys Glu Trp Ser
785                 790                 795                 800

Ala Lys Tyr Phe Asn Gly Thr Asn Ile Leu His Arg Gly Ala Gly Tyr
                805                 810                 815

Val Leu Arg Ser Asn Asp Gly Lys Tyr Tyr Asn Leu Gly Thr Ser Thr
                820                 825                 830

Gln Gln Phe Leu Pro Ser Gln Leu Ser Val Gln Asp
            835                 840
```

METHODS FOR THE ENZYMATIC MODIFICATION OF STEVIOL GLYCOSIDES, MODIFIED STEVIOL GLYCOSIDES OBTAINABLE THEREBY, AND THE USE THEREOF AS SWEETENERS

RELATED APPLICATION DATA

This application is a National Stage Application under 35 U.S.C. 371 of co-pending PCT application number PCT/NL2016/050172 designating the United States and filed Mar. 10, 2016; which claims the benefit of EP application number 15158421.6 and filed Mar. 10, 2015 each of which are hereby incorporated by reference in their entireties.

The present invention relates generally to the production of steviol glycosides. Particularly, the invention relates to methods for the enzymatic modification of steviol glycosides to novel steviol glycosides, and use thereof as sweeteners.

Sweeteners are well known as ingredients used most commonly in the food, beverage, or confectionary industries. The sweetener can either be incorporated into a final food product during production or for stand-alone use, e.g. when appropriately diluted or as a tabletop sweetener. Sweeteners include natural sweeteners such as sucrose, high fructose corn syrup, molasses, maple syrup, and honey and artificial sweeteners such as aspartame, saccharine and sucralose.

The leaves of the herb plant *Stevia rebaudiana* Bertoni, a rhizomatous perennial shrub of the Asteraceae [Compositae] family, contain a high variety of natural sweet compounds, being steviol glycosides (Brandle et al. 1998). Stevioside (5-10% w/w of dried leaves) and Rebaudioside A (2-4% w/w of dried leaves) are the most abundant and they taste about 200-300 times sweeter than sucrose (0.4% water solution). Therefore, they can be considered as "bio" alternatives for sucrose and for artificial (synthetic) sweeteners (Geuns 2003; Goyal et al. 2010; Puri et al. 2011).

In addition to sweetness, some steviol glycosides, in higher doses and regular consumption, possess diverse pharmacological properties, like antioxidant, antibacterial, antifungal, antiviral, antitumor, gastro protective (antidiarrheal), and they seem to have a positive effect on renal function, blood pressure and blood glucose levels (Chatsudthipong and Muanprasat 2009; Madan et al. 2010; Brahmachari et al. 2011; Lemus-Mondaca et al. 2012; Shivanna et al. 2013). They can be of benefit to people suffering from obesity, diabetes mellitus, hypertension, phenylketonuria, heart disease and dental caries (Yadav and Guleria 2012). Steviol glycosides are non-caloric, not carcinogenic, not genotoxic and not associated with any reproductive/developmental toxicity in humans (European Food Safety Authority, 2010).

Structurally, steviol glycosides have an ent-13-hydroxykaur-16-en-19-oic acid as aglycone but differ in carbohydrate composition (see FIG. 1).

The ratio of the number of glucose units at the 13-tert-hydroxyl group to that at 19-carboxyl group seems to have a relationship with the sweetness as well as with the quality of taste of the steviol glycosides (Darise et al. 1984). For instance, Rebaudioside A is less bitter than Stevioside. Enzymatic glucosylation studies of Stevioside show that the glycosidic linkage specificity affects the organoleptic properties of steviol glycosides as well. Fukunaga et al. (1989) found that both mono- and di-($\alpha 1 \rightarrow 4$)-glucosylation of Stevioside at the C-13-position gave products with remarkable improvement in both the intensity and quality of the sweetness. However, both mono- and di-($\alpha 1 \rightarrow 4$)-glycosylation at the C-19 position resulted in an increased bitter aftertaste and a lower sweetness intensity (Fukunaga et al. 1989). On the other hand, attachment of an $\alpha$-linked glucose to the C-6 hydroxyl group of the glucose unit at the C-19-position led to a remarkable improvement in the quality of taste (Lobov et al. 1991). Apparently, the anomericity of the glycosidic bond does not influence sweet and bitter taste perception to a great extent, since several recent studies show that Rebaudioside D and Rebaudioside M, both Rebaudioside A derivatives with respectively one and two $\beta$-linked glucose units extra at the 19-O-glucosyl moiety, both have a more desirable taste profile than Rebaudioside A and many other steviol glycosides (Hellfritsch et al. 2012; US 2013/00771521A1; WO2014/122227; Prakash et al. 2014). Compared to Rebaudioside A, Rebaudioside D has increased sweetness and decreased bitterness in water and in carbonated beverage base. Rebaudioside M showed reduced bitterness compared to Rebaudioside A but similar sweetness intensity in water solution. In acidified water a reduced bitterness and higher sweetness were perceived compared to Rebaudioside A (Prakash et al. 2014). Moreover, attachment of an ($\alpha 1 \rightarrow 2$)- or an ($\beta 1 \rightarrow 2$)-(is Rebaudioside E)-linked glucose to the C-2 hydroxyl group of the glucose unit at the C-19-position of Stevioside improved the organoleptic products of Stevioside, yielding compounds with similar sweetness, but with reduced bitterness (Ye et al. 2013).

The main drawback for successful commercialization of *Stevia* sweeteners is their slight bitterness and astringency (Stevioside in particular). These undesirable properties can be reduced or eliminated by modifying the glycosyl moieties of the steviol glycosides.

Chemical modifications of steviol glycosides have been performed with the aim of improving the quality of taste of these compounds. For instance, Stevioside and Rebaudioside A could be improved by replacement of the 19-O-glucosyl residues by a (sodiosulfo)propyl [$(CH_2)_3SO_3Na$] moiety (DuBois et al. 1981; DuBois and Stephenson 1985). Furthermore, several analogs of stevioside have been synthesized by replacing the C-19-O-$\beta$-D-glucosyl moiety for another monosaccharide (e.g. $\beta$-D-Xyl, $\alpha$-L-Ara, $\alpha$-D-Man, or $\alpha$-L-Rha) or extension of the C-19 $\beta$-D-glucosyl moiety with a monosaccharide ($\alpha$-L-Rha or $\alpha$-L-Qui). However, it is generally held that the application of chemical methods to modify steviol glycosides is impractical, due to the need of multistep sequences in the selective protection-deprotection synthesis strategies. Furthermore, the use of organic solvents and metallic salts will cause problems for acceptation of the obtained derivatives in the food industry. To overcome these problems, biocatalyst alternatives are more preferred, also with the objectives of "green" chemistry.

A promising procedure is to subject steviol glycosides to the reaction of enzymatic transglycosylation, thereby introducing new monosaccharide residues into the molecule. Depending on the number, position and anomericity of the monosaccharide residues, the taste quality and potency of the compounds will vary.

To improve the taste, enzymatic modifications of the carbohydrate moieties of steviol glycosides have been performed by using different enzyme systems, amongst which UDP-glucosyltransferases (UGTases)(WO2013/176738A9; WO 2014/122227) and cyclodextrin glucanotransferases (CGTases) (Darise et al 1984; Li et al 2013; US2014/0227421A1). UGTases are efficient enzymes with high regio-specificity, catalyzing the transfer of $\alpha$- or $\beta$-linked glucoses at a specific location. However, UGTases require expensive nucleotide activated sugars as glycosyl donor, which makes them less attractive for industrial applications.

CGTases catalyze coupling and disproportionation reactions, transferring glucose residues from starch or cyclodextrins to acceptor molecules. The intermolecular transglucosylation reaction is expected to occur exclusively at the C-4-hydroxyl group of the non-reducing-end glucose residues of the steviol glycosides due to the acceptor specificity of the CGTase enzyme. Although often high yields are obtained, CGTase has poor C-13/C-19 regio-specificity producing steviol glycosides that are mostly mixtures of compounds with α-D-glucosyl extensions at C-13 and C-19. Furthermore, the (α1→4)-linkages introduced by CGTase enzymes are rapidly hydrolyzed in the human mouth by the amylolytic enzymes present in saliva, thereby increasing the caloric content of steviol glycosides. Introduction of α-amylase resistant glycosidic linkages, such as the (α1→6) and (α1→3) linkages, is therefore more desirable, since it will answer the consumers demand for low and zero calorie food products.

Accordingly, the present inventors aimed for novel means and methods to provide enzymatically modified steviol glycosides. In particular, they set out to develop an enzymatic method yielding compounds showing a reduced bitterness and/or higher sweetness compared to the unmodified steviol glycoside. Preferably, the method is economically attractive at an industrial scale, and preferably does not require expensive nucleotide activated sugars as glycosyl donor.

To that end, they screened the glucosylation potential of glucansucrase and fructansucrase enzymes of different lactobacilli, of which most members have the generally-recognized-as-safe (GRAS) status, such as *Lactobacillus reuteri*. Glucansucrases are extracellular enzymes, which are only reported to occur in lactic acid bacteria. They synthesise α-glucan polymers from the cheap donor substrate sucrose. Depending on the glucansucrase enzyme, different (mixtures of) glycosidic linkages are introduced in their glucan products, namely (α1→2)-, (α1→3)-, (α1→4)- and (α1→6)-linkages (Leemhuis et al. 2013). The low cost of the glucosyl donor substrate sucrose used by glucansucrase enzymes is a major advantage for their industrial applications. Most importantly, the (α1→2)-, (α1→3)- and (α1→6)-linkages introduced by glucansucrase enzymes are not hydrolyzed in the mouth by the amylolytic enzymes present in saliva. More than 100 enzymes consisting of wild-type and mutant glucansucrase and fructansucrase enzymes with different product specificity from different *Lactobacillus reuteri* strains, were screened for their ability to glucosylate the steviol glycoside Rebaudioside A. Rebaudioside A glucosides were isolated by semi-preparative NP-HPLC and their structures were elucidated by MALDI-TOF mass spectrometry and 1D/2D $^1$1-1/$^{13}$C NMR spectroscopy. Sensory evaluations were performed to determine the taste attributes of the novel Rebaudioside A glucosides.

It was surprisingly found that only the glucansucrase GTF180 from *Lactobacillus reuteri* 180 (GenBank accession number AY697430) was able to glucosylate Rebaudioside A. NMR structural analysis of the Rebaudioside A glucosylation products showed that GTF180 specifically and only glucosylates Rebaudioside A at the C-19 β-linked glucose residue. Interestingly, several GTF180 point mutants displayed much higher transglucosylating activity towards Rebaudioside A. One mutant, Q1140E, even showed ~96% Rebaudioside A conversion. Similar results were observed with respect to modification of Stevioside.

Accordingly, in one embodiment the invention provides a method for enzymatically providing a modified steviol glycoside, comprising incubating a steviol glycoside substrate in the presence of a glucose donor and the glucansucrase GTF180 of *Lactobacillus reuteri* strain 180, or a mutant thereof having the desired transglycosylation activity.

To our knowledge there is only one report on glucosylation of stevioside using glucansucrases. Musa et al. reported the enzymatic modification by alternansucrase from *Leuconostoc citreum* SK24.002 in the biotransformation of stevioside to fully or partially remove the bitter taste of the stevioside. With optimized reaction conditions a maximum transglucosylation yield of 43.7% was achieved with stevioside. Stevioside glycosides with 1 to 3 α-glucose units attached were obtained. In a follow-up study the structure of the product was characterized to be 13-{[α-D-glucopyranosyl-(1→3)-α-D-glucopyranosyl-(1→6)-α-D-glucopyranosyl-(1→3)-β-D-glucopyranosyl-(1→2)-β-D-glucopyranosyl] oxy}ent-kaur-16-en-19-oic acid β-D-glucopyranosyl ester (Musa et al. 2014). Thus, the method of Musa et al. uses a distinct enzyme, shows a lower yield and results in a distinct type of modification, namely α-glucosylation at the C-13 site instead of at the C-19 site.

In one embodiment of the present invention, the steviol glycoside is modified with at least one α-glucose residue at the C-19 β-linked glucose residue. For example, the steviol glycoside is provided with one or more glucoses via an (α 1→6), an (α 1→3) glycosidic bond, or a combination thereof. In a specific aspect, the modification involves the addition of one glucose via an (α 1→6) glycosidic bond (β-isomaltose) or an (α 1→3) glycosidic bond (β-nigerose) (FIG. 5A). In another specific aspect, the modification involves the addition of a glucosyl-glucose unit via an (α1→6) glycosidic bond at the β-linked glucose. Within the unit, the glucose residues can be connected via an (α1→6) glycosidic bond (isomaltose) or an (α1→3) glycosidic bond (nigerose) (FIGS. 5B and 5C).

A steviol glycoside can be modified at multiple positions. For example, modifications can occur at the C-13 and/or the C-19 position(s) of the steviol aglycone. In view of the attractive taste characteristics of Rebaudioside D and Rebaudioside M, the steviol glycoside is preferably at least modified at the C-19 site of the steviol glycoside.

More preferably, the modified steviol glycoside is only modified at the C-19 site of the steviol glycoside. For example, in one embodiment the invention provides a method for the enzymatic production of a modified steviol glycoside, which is only modified with a single glucose residue at the C-19 position of the steviol aglycone. In one embodiment, the modification comprises the addition of a single (α1→6) glucose at the C-19 β-linked glucose residue.

The steviol glycoside substrate can be of any type. For example, it is selected from the group consisting of Stevioside, Rubusoside, Rebaudiosides including Rebaudioside A, Rebaudioside C, Rebaudioside D, and Rebaudioside E, and Dulcoside compounds. In one embodiment, the steviol glycoside substrate has at least one monosaccharide moiety at the C-19 position of the steviol glycoside.

In one specific embodiment, the steviol glycoside substrate is a Rebaudioside. The present inventors hypothesized that α-glucosylation of Rebaudioside A at the C-19 site could thus yield Rebaudioside D and Rebaudioside M anomeric isomers with a similar or even better taste profile than Rebaudioside D and Rebaudioside M. Accordingly, in a preferred embodiment, the invention provides a method for enzymatic modification of Rebaudioside A [13-({β-D-glucopyranosyl-(1→2)-[β-D-glucopyranosyl-(1→3)-]β-D-glucopyranosyl}oxy)ent-kaur-16-en-19-oic acid α-D-glucopyranosyl ester].

In another specific embodiment, the steviol glycoside substrate is Stevioside, the most abundant and one of the bitterest tasting steviol glycosides present in *Stevia* extracts.

Typically, on a dry weight basis, the four major steviol glycosides found in the leaves of *Stevia* are Dulcoside A (0.3%), Rebaudioside C (0.6-1.0%), Rebaudioside A (2-4%) and Stevioside (5-10%). Other glycosides identified in reasonable amounts in *Stevia* extract include Rebaudioside B, D, E, and F, Steviolbioside and Rubusoside. Among these, only Stevioside and Rebaudioside A are currently available on a commercial scale.

Steviol glycosides can be extracted from leaves using methods known in the art, typically involving either water or organic solvent extraction. Supercritical fluid extraction and steam distillation methods have also been described. Methods for the recovery of diterpene sweet glycosides from *Stevia rebaudiana* using supercritical $CO_2$, membrane technology, and water or organic solvents, such as methanol and ethanol, may also be used.

US2014/343262 discloses a method for purifying steviol glycosides, comprising the steps of: a. passing a solution of steviol glycosides through a multi-column system including a plurality of columns packed with adsorbent resin, to provide at least one column having adsorbed steviol glycosides; and b. eluting fractions with low Rebaudioside X (was later named as Rebaudioside M (US 2014/0227421; Prakash et al 2014) content from at least one column having adsorbed steviol glycosides to provide an eluted solution comprising steviol glycosides.

Rebaudioside A is generally available at ≤80% purity. The primary impurities comprise Stevioside, Steviolbioside, Rebaudioside B, Rebaudioside C, Rebaudioside D, Dulcoside A, Rebaudioside F, and other steviol glycosides. Many studies focused on the recovery of a high purity of Rebaudioside A in high recovery. U.S. Pat. No. 5,962,678 discloses the re-crystallization of Rebaudioside A using an anhydrous methanol solution to obtain an 80% pure Rebaudioside A. By repeating the re-crystallization with anhydrous methanol numerous times, the purity of rebaudioside A may be increased to over 95%. US 2006/0083838 discloses purification of Rebaudioside A through re-crystallization with a solvent comprising ethanol and between 4 and 15% water. Japanese Patent Application No. 55-23756 discloses a method for purifying rebaudioside A and stevioside by crystallization from aqueous ethanol (>70%) to obtain an 80% pure Rebaudioside A. US 2007/0082103 discloses a method for purifying Rebaudioside A by recrystallization from aqueous ethanol, asserting a two-step recrystallization from crude Rebaudioside (60%) results in the formation of at least 98% pure Rebaudioside A at 97% yield. U.S. Pat. No. 8,791,253 provides a substantially pure Rebaudioside A composition using only a single recrystallization step.

The concentration of steviol glycoside substrate in a method of the invention can vary e.g. depending on type of substrate, desired modification, etc. Typically, the reaction mixture comprises at least 20 mM steviol glycoside to be modified, preferably at least 30 mM, more preferably at least 50 mM, like 60, 70, 80 90 to100 mM. The maximal concentration is among others dependent on the substrate solubility in an aqueous reaction medium. For example, good results were obtained using 50 to 100 mM Rebaudioside A or Stevioside as substrate.

A method of the invention uses sucrose as glucose donor. Sucrose is cheap and widely available. Good results were obtained when sucrose is used at a concentration of at least 50 mM, preferably at least 100 mM, more preferably at least 500 mM. For example, the reaction mixture comprises at least 500 mM, 600 mM, 700 mM, 800 mM, 900 mM or 1 M sucrose. Even higher concentrations, like up to 2 M or 3 M, may be used. The glucose donor can in its total amount be added at the onset of the reaction. In some embodiment, it is advantageous to add sucrose in a batch wise manner. For example, sucrose is added in a batch wise manner, e.g. at the onset, after 1.5 and 3 hours, to a final amount of at least 1 M, more preferably at least 2 M.

The reaction is typically performed at a temperature of about 20 to 70° C., in the pH range of 3-7. Preferably, a temperature of about 37° C. is used.

The reaction is allowed to proceed until a desirable amount of modified steviol glycoside is produced. Typically, incubations are performed during a period ranging from about 1 hour to overnight.

The skilled person will be able to determine the amount of GTF180 glucansucrase enzyme to be used to obtain a desirable degree of enzymatic modification under the given reaction conditions. For example, 1 to 50 U/mL can be used. Preferably, at least 3 U/mL is used. For economical reasons, it may be advantageous to use up to 35 U/mL. In one embodiment, 5 to 30 U/mL is used. One unit (U) of enzyme is defined as the amount of enzyme required for producing 1 μmol monosaccharide per minute in a reaction mixture containing 25 mM sodium acetate (pH 4.7); 1 mM $CaCl_2$; and 1 M sucrose at 37° C.

In one embodiment, wild-type GTF180 glucansucrase from *Lactobacillus reuteri* strain 180 is used (GenBank accession number AY697430). In another embodiment, a mutant GTF180 glucansucrase is used. As used herein, a mutant GTF180 glucansucrase refers to an enzyme comprising one or more amino acid substitutions, amino acid deletions and/or amino acid insertions as compared to the wild type amino acid sequence.

In a preferred embodiment, a GTF180 mutant for enzymatic modification of a steviol glycoside according to the present invention comprises a substitution mutation at positions S1137, Q1140, L981 and/or W1065 (numbering based on the GenBank sequence AY697430). Preferably, the mutation is a non-conservative substitution i.e. a mutation that results in an amino acid change that has different properties than the native amino acid. For example, said mutant has one or more of the following amino acid substitutions: S1137Y, Q1140E, L981A, W1065L/E/Q/F.

Figure 3:
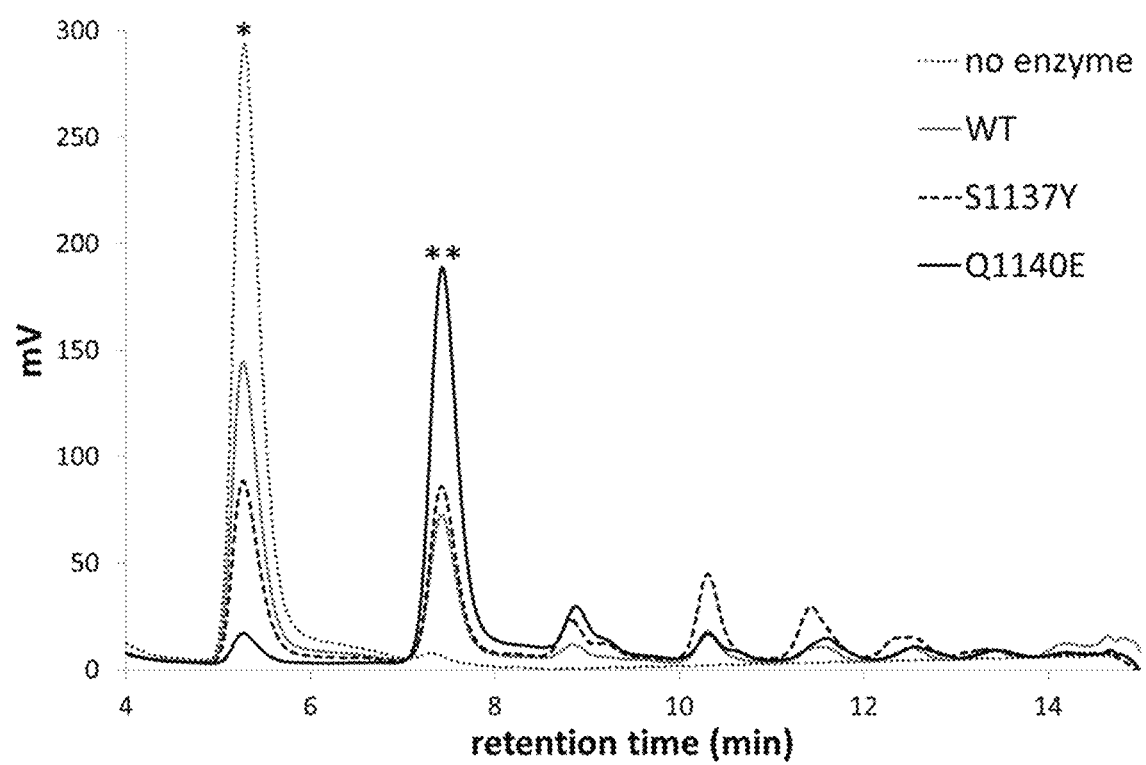
Figure 4A:
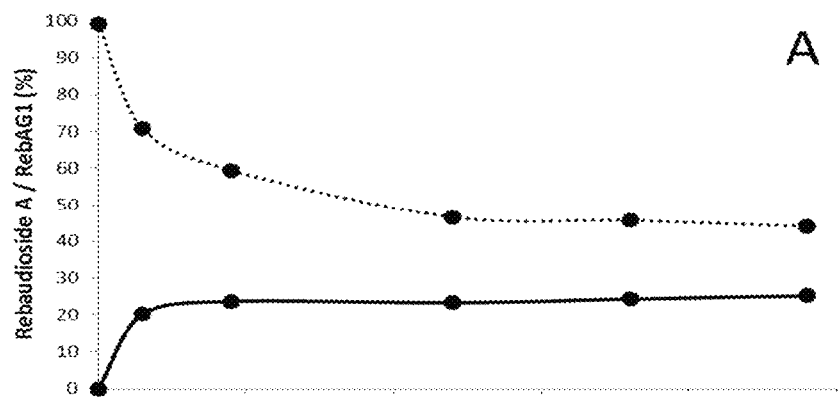
Figure 4B:
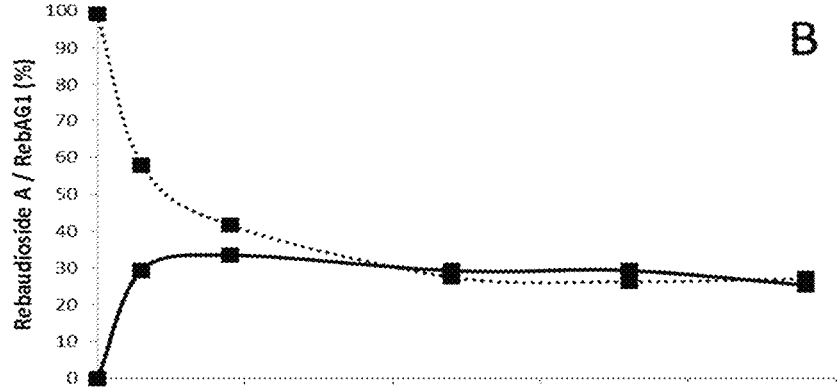
Figure 4C:
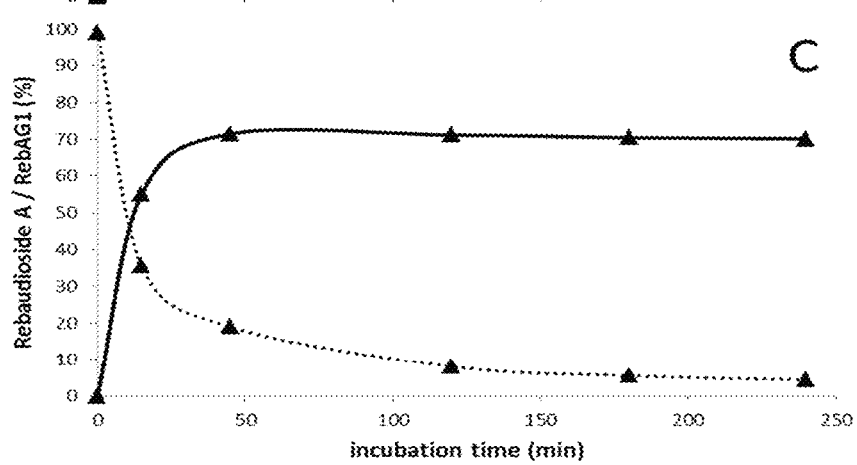

In another embodiment, a mutant GTF180 is a deletion mutant or truncated variant, wherein a stretch of at least 10 amino acids is removed from the N- and/or C-terminus. In one aspect, the truncation mutant is GTF180-ΔN comprising residues 742-1772, in which the N-terminal variable domain has been deleted. For example, good results were obtained with GTF180-ΔN which is the 117 kDa N-terminally truncated (741 residues) fragment of the GTF180 full-length wild type protein. GTF180-ΔN is fully active and produces an α-glucan polymer with similar size and linkage distribution as the full length enzyme (Kralj et al. 2004a). NMR structural analysis of the Rebaudioside A glucosylation products showed that GTF180-ΔN specifically and only glucosylates Rebaudioside A at the C-19 β-linked glucose residue. Interestingly, several GTF180-ΔN substitution mutants displayed much higher transglucosylating activity towards Rebaudioside A than GTF180-ΔN. One mutant, Q1140E, even showed 96% Rebaudioside A conversion compared to ~55% Rebaudioside A conversion by GTF180-ΔN (FIG. 3 and FIG. 4). Accordingly, in a preferred embodiment a method of the invention uses GTF180-ΔN with one or more amino acid substitutions, for example at position Q1140, S1137, L981, and/or W1065. Specific exemplary mutant enzymes include GTF180-ΔNQ1140E, GTF180-ΔNQ1140F, GTF180-ΔNQ1140N, GTF180-ΔNQ1140Y, GTF180-ΔNQ1140R, GTF180-ΔNS1137Y, GTF180-ΔN L981A, GTF180-ΔN W1065L, GTF180-ΔN W1065E, GTF180-ΔN W1065 Q and GTF180-ΔN W1065F.

In another aspect, the truncation mutant is GTF180-ΔNΔV, in which both the N-terminal variable domain and N-terminal domain V fragment (corresponding to the first 793 N-terminal amino acids), and the domain V C-terminal fragment (corresponding to the last 136 C-terminal amino acids) have been deleted (Meng et al. 2015a) to result in a GTF180 mutant consisting of amino acids 794-1636. This GTF180-ΔNΔV truncation mutant, which may be considered as the "catalytic core", has a ~50% reduction in size compared to the full length GTF180 wild type, is fully active, creates a similar glycosidic linkage distribution as GTF180 wild type, but is heavily impaired in high-molecular-mass polysaccharide synthesis.

A truncation mutant of the invention may additionally contain substitution mutation(s), e.g. to improve its catalytic properties. In one embodiment, the mutant is GTF180-ΔNΔV, furthermore comprising a substitution mutation at position(s) S1137, Q1140, L981 and/or W1065. For example, said mutant has one or more of the following amino acid substitutions: S1137Y, Q1140E, L981A, W1065L/E/Q/F. Specific exemplary mutant enzymes include GTF180-ΔNΔVQ1140E, GTF180-ΔNΔVQ1140F, GTF180-ΔNΔVQ1140N, GTF180-ΔNΔVQ1140R GTF180-ΔNΔVQ1140Y, GTF180-ΔNΔVS 1137Y, GTF180-ΔNΔV L981A, GTF180-ΔNΔV W1065L, GTF180-ΔNΔV W1065E, GTF180-ΔNΔV W1065 Q and GTF180-ΔNΔV W1065F.

Mutant GTF180 glucansucrases have for example been described by Van Leeuwen et al. reporting the mutagenesis of specific amino acid residues of the GTF180-ΔN enzyme, which yielded 12 mutant enzymes that produce modified exopolysaccharides (mEPSs) from sucrose (van Leeuwen et al. 2009). It was found by the present inventors that two of the single mutants, Q1140E and S1137Y of GTF180-ΔN, displayed much higher transglucosylating activity towards Rebaudioside A than GTF180-ΔN, showing respectively ~96% and ~73% Rebaudioside A conversion compared to ~55% Rebaudioside A conversion by GTF180-ΔN (FIG. 3 and FIG. 4). Mutant Q1140E mainly produced mono-α-glucosylated Rebaudioside A, while GTF180-ΔN and mutant S1137Y produced multiple-α-glucosylated forms with DP up to at least 8. NMR structural analysis of the α-glucosylated products showed that GTF180-ΔN and mutants Q1140E and S1137Y specifically and only glucosylate Rebaudioside A at the C-19 site. The three enzymes glucosylated Rebaudioside A exclusively with an (α1→6)-linked glucose at the C-19 β-linked glucose, yielding RebAG1. The di-glucosylated Rebaudioside A products of GTF180-ΔN and mutant S1137Y were both elongations of RebAG1 with an (α1→3)-linked glucose (~75%) or another (α1→6)-linked glucose (~25%) coupled at the terminal α-glucose residue. Accordingly, specifically preferred mutants include Q1140E and S1137Y of GTF180-ΔN.

GTF180-ΔN mutants L981A and W1065L/E/Q/F (Meng et al. 2015b) are able to α-glucosylate Rebaudioside A, but show almost no polymerization (i.e. oligosaccharide and glucan formation) activity. This is a clear advantage during downstream processing, the purification of elongated Rebaudioside A products from mono- and disaccharides, oligosaccharides and glucans. By eliminating α-glucan synthesis, the most important side reaction, higher glycosylation yields were obtained for Rebaudioside A. At 200 mM sucrose and 1.5 hour incubation time, these mutants have similar or even higher transglucosylating activity than GTF180-ΔN and mutants Q1140E and S1137Y on Rebaudioside A. As observed with Rebaudioside A as acceptor molecule, mutant Q1140E also converted Stevioside mainly into one mono-α-glucosylated product. Hence, in one embodiment the mutant enzyme comprises the mutation L981A and/or W1065L, W1065E, W1065Q, W1065F.

Also provided herein is the use of glucansucrase GTF180 of Lactobacillus reuteri strain 180 or a mutant thereof having the desired transglycosylation activity to enhance or improve the organoleptic properties of a steviol glycoside, for example to fully enhance the sweetness, partially remove the bitter taste and/or aftertaste of a steviol glycoside, preferably of Rebaudioside A or Stevioside.

In the screening of substitution mutants useful for modifying Rebaudioside A, it was observed that the reaction mixture comprising an inactive mutant or enzyme that is unable to α-glucosylate Rebaudioside A turned cloudy due to the gradual precipitation of Rebaudioside A in time, whereas those comprising an active enzyme able to α-glucosylate Rebaudioside A remained clear. Without wishing to be bound by theory, the addition of glucose moieties to Rebaudioside A increases its solubility. This phenomenon allows the rapid selection of active mutants by evaluating the appearance of the reaction mixture, preferably after ~6 hours of incubation in case of a final Rebaudioside A concentration at a minimum of 50 mM and ~16 hours of incubation in case of a final Rebaudioside A concentration at a minimum of 30 mM. For example, when the reactions are performed in a microtiter plate or other type of transparent container, a mere visual inspection can be sufficient to identify one or more mutants for further characterization.

Accordingly, the invention also provides a method for identifying a glucansucrase capable of modifying a steviol glycoside, preferably Rebaudioside A or Stevioside, comprising the steps of:

a) generating a panel of mutants of GTF180 of Lactobacillus reuteri strain 180;

b) incubating each mutant with a steviol glycoside in the presence of a glucose donor in an aqueous reaction mixture under conditions allowing for glycosylation of the steviol glycoside; and c) selecting at least one mutant of GTF180 of Lactobacillus reuteri 180 capable of modifying the steviol glycoside, by determining its capacity to at least partially prevent the reaction mixture from becoming cloudy;

d) optionally further determining the structure of the modified steviol glycoside and selecting a mutant GTF180 of Lactobacillus reuteri 180 capable of modifying the C-19 site of the steviol glycoside.

Preferably, the mutant panel is prepared starting from a truncated GTF180 enzyme, like the truncated variant lacking the N-terminal variable domain (GTF180-ΔN), and/or the N- and C-terminal domain V fragments (GTF180-ΔNΔV).

In one embodiment, the panel of mutants comprises different substitution mutants, preferably non-conservative substitution mutants. For example, the screening method comprises creating a panel of GTF180 (truncation) mutants with different (non-conservative) amino acid substitutions at the Q1140 position and testing all the Q1140 mutants for steviol glycoside α-glucosylation. See FIG. 8 herein below.

A further aspect of the invention relates to a modified steviol glycoside obtainable by a method according to the invention. In one embodiment, the steviol glycoside is modified with at least one glucose residue. In a specific aspect, the modification involves the addition of one glucose via an (α 1→6) glycosidic bond (β-isomaltose) (FIG. 5A). In another specific aspect, the modification involves the addition of a glucosyl-glucose unit via an (α1→6) glycosidic bond at the β-linked glucose. Within the unit, the glucose residues can be connected via an (α1→6) glycosidic bond (isomaltose) or an (α1→3) glycosidic bond (nigerose) (FIGS. 5B and 5C).

The invention preferably provides a steviol glycoside modified at the C-19 site of the steviol glycoside. More preferably, the modified steviol glycoside is only modified at the C-19 site of the steviol glycoside. For example, in one embodiment the invention provides a modified steviol glycoside which is only modified with a single α-glucose residue at the C-19 site of the steviol glycoside. In one embodiment, the C-19 site is modified with a single (α1→6) linked glucose.

An exemplary modified steviol glycoside of the invention is selected from the group consisting of
(i) 13-({β-D-glucopyranosyl-(1→2)-[β-D-glucopyranosyl-(1→3)-]β-D-glucopyranosyl}oxy)ent-kaur-16-en-19-oic acid α-D-glucopyranosyl-(1→6)-β-D-glucopyranosyl ester (FIG. 5A)
(ii) 13-({β-D-glucopyranosyl-(1→2)-[β-D-glucopyranosyl-(1→3)-]β-D-glucopyranosyl}oxy)ent-kaur-16-en-19-oic acid α-D-glucopyranosyl-(1→6)-α-D-glucopyranosyl-(1→6)-β-D-glucopyranosyl ester (FIG. 5B)
(iii) 13-({β-D-glucopyranosyl-(1→2)-[β-D-glucopyranosyl-(1→3)-]β-D-glucopyranosyl}oxy)ent-kaur-16-en-19-oic acid α-D-glucopyranosyl-(1→3)-α-D-glucopyranosyl-(1→6)-β-D-glucopyranosyl ester (FIG. 5C)

Figure 7:
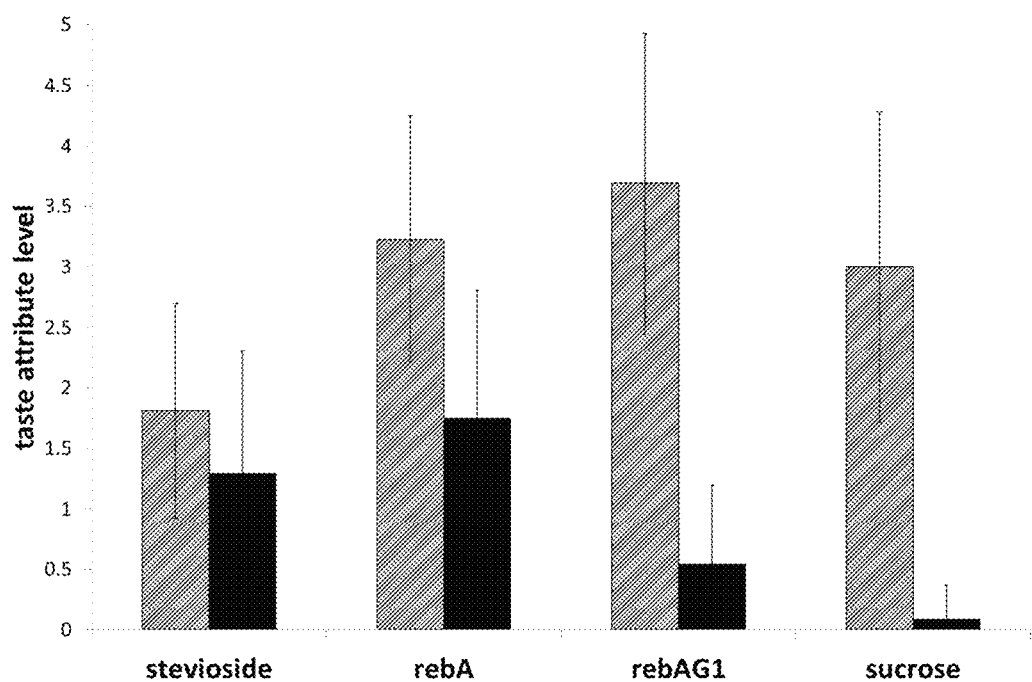

To determine the effect of (α1→6) glucosylation at the 19-O-glucosyl moiety of Rebaudioside A on sweetness and bitterness of Rebaudioside A, a taste evaluation was performed in which one of the novel Rebaudioside A glucosides, i.e. (i) 13-({β-D-glucopyranosyl-(1→2)-[β-D-glucopyranosyl-(1→3)-]β-D-glucopyranosyl}oxy)ent-kaur-16-en-19-oic acid α-D-glucopyranosyl-(1→6)-β-D-glucopyranosyl ester, was compared to Rebaudioside A. For this, in a blind test, twelve test persons that were able to perceive the bitter aftertaste of steviol glycosides were asked to rate sweetness and bitterness on a scale from 0 to 5, scoring 0 indicating not sweet/not bitter and 5 indicating very sweet/very bitter. A clear trend was observed showing that the novel Rebaudioside A glucoside had an increased and more natural sweetness and reduced bitterness compared to Rebaudioside A (FIG. 7).

Also provided is the use of a modified steviol glycoside according to the invention as low-glycemic sweetener, and a method for sweetening a consumable, comprising including in said consumable an effective amount of the modified steviol glycoside, optionally combined with other edible ingredient, sweetener and/or sweetness enhancer.

A further aspect relates to a sweetening composition comprising at least one modified steviol glycoside as provided herein. In certain embodiments the sweetener composition is a table top sweetener suitable to be used in cooking or to be added by a consumer to a beverage or other food. Such sweetener composition can be packaged and sold in bulk. Alternatively, in certain embodiments the sweetener composition is packaged in single serving packets to be opened at the time of use by the consumer. The at least one other edible ingredient of the sweetener composition, in accordance with certain embodiments, may, for example, be a flavorant, e.g., flavorant below its threshold perception level or in an amount readily perceptible to the consumer, a flowing agent, a coloring agent, a bulking agent to provide ease of handling and/or improved mouthfeel in beverages and other food products in which the sweetener composition is used, and/or other suitable ingredient, or a combination of any two or more of them. In certain embodiments the bulking agent(s) can provide an improved sweetness profile by increasing the up-front sweetness provided by the sweetener composition. In certain embodiments the at least one other edible ingredient is erythritol, D-tagatose, and/or D-psicose, for example a combination of two or more of those ingredients is included in the sweetener composition, such as erythritol and D-tagatose, or erythritol and D-psicose, or D-tagatose and D-psicose.

Also provided is a consumable comprising at least one modified steviol glycoside according to the invention, optionally combined with another sweetener and/or sweetness enhancer. For example, the consumable is selected from the group of beverages, foodstuff, an oral care product, a tobacco product, a pharmaceutical products and nutraceutical products.

Typically, a foodstuff comprises a sweetening amount of a modified steviol glycoside of the invention, and at least one other food ingredient. As used herein, the term "food ingredient" means any edible substance suitable to provide flavor, nutrition, color, bulk, texture or other mouthfeel, stability, acidity, thickening, anti-caking or the like, or a combination of any two or more of these. As further discussed below, exemplary food ingredients suitable for use in the novel food products disclose here include grain components, carbonated or non-carbonated water, other sweeteners, e.g., a sweetening amount of at least one nutritional sweetener, flavorants, acidulants, colorants, bulking agents, etc. In certain exemplary (i.e., non-limiting) embodiments, the food product is packaged in a single serving quantity. The food products of this aspect of the disclosure include, for example, solid foods, gels, beverages, etc.

Examples of suitable sweeteners and sweetness enhancers include sucrose, fructose, glucose, high fructose corn syrup, corn syrup, xylose, arabinose, rhamnose, erythritol, xylitol, mannitol, sorbitol, inositol, acesulfame potassium, aspartame, neotame, sucralose, and saccharine, and mixtures thereof; trilobatin, hesperetin dihydrochalcone glucoside, naringin dihydrochalcone, mogrosides including mogroside V, Luo Han Guo extract, rubusoside, rubus extract, glycyphyllin, isomogroside V, mogroside IV, siamenoside I, neomogroside, mukuroziside lib, (+)-hernandulcin, 4 β-hydroxyhemandulcin, baiyunoside, phlomisoside I, bryodulcoside, bryoside bryonoside, abrusosides A-E, cyclocarioside A, cyclocaryoside I, albiziasaponins A-E, glycyrrhizin, araboglycyrrhizin, periandrins I-V, pterocaryosides A and B, osladin, polypodosides A and B, telosmoside A8-18, phyllodulcin, huangqioside E neoastilbin, monatin, 3-acetoxy-5,7-dihydroxy-4'-methoxyflavanone, 2R,3R-(+)-3-Acetoxy-5,7,4'-trihydroxyflavanone, (2R.3R)-dihydroquercetin 3-O-acetate, dihydroquercetin 3-O-acetate 4-methyl ether, brazzein, curculin, mabinlin, monellin, neoculin, pentadin, thaumatin, and combinations thereof. Some of the compounds listed above are known sweetness enhancers as well as sweeteners. When used as sweetness enhancers they are normally used below their sweetness detection thresholds.

The beverages include, for example, juice beverages (e.g., beverages comprising one or more fruit juices and/or one or more vegetable juices), hydration beverages, carbonated soft drinks (CSDs), frozen beverages, frozen carbonated beverages, diet or other reduced calorie beverages, etc. It will be recognized by those skilled in the art that there is overlap between these categories. As used herein, "reduced calorie beverage" means a beverage having at least a 25% reduction in calories per 8 oz. serving of beverage as compared to the full calorie version, typically a previously commercialized full-calorie version (e.g., wherein substantially all of the sweetening comes from a nutritive sweetener, such as sucrose, HFCS or the like). In at least certain embodiments, a reduced calorie beverage has about a 50% reduction in calories per 8 oz. serving as compared to the full calorie version. As used herein, a "low-calorie beverage" has fewer than 40 calories per 8 oz. serving of beverage. As used herein, "zero-calorie" or "diet" means having less than 5 calories per serving, e.g., per 8 oz. for beverages.

According to another aspect, beverage products are provided that comprises water, and acidulant component comprising at least one acid, a flavoring component comprising at least one flavoring ingredient, and a sweetener component comprising a sweetening amount of modified steviol glucoside, and optionally a sweetening amount of one or more other sweeteners. In certain exemplary embodiments of the beverage products according to this aspect, the beverage products are ready-to-drink beverages having a pH higher than 3.0 and lower than 4.0. Such ready-to-drink beverages may, for example, be hydration beverages, also referred to as sports drinks, having added electrolytes. In other exemplary embodiments the ready-to-drink beverages are carbonated soft drinks, for example reduced calorie or diet cola beverages. In certain exemplary embodiments of the beverage products according to this aspect, the beverage products are syrups suitable to be diluted, for example, by a 1-plus-5 throw with carbonated or un-carbonated water to produce a ready-to-drink beverage.

According to certain embodiments, the modified steviol glycoside of the invention provides at least 10% of the total sweetening of the consumable, e.g. a diet cola syrup, a ready-to-drink diet cola beverage, another beverage product, or another food product in accordance with the present disclosure. According to certain embodiments, it provides at least 20% of the total sweetening, or at least 30% of the total sweetening, or at least 40% of the total sweetening, or at least half of the total sweetening, or at least 60% of the total sweetening, or at least 70% of the total sweetening, or at least 80% of the total sweetening, or at least 90% of the total sweetening. Optionally every additional sweetener ingredient is an organic sweetener. Optionally every sweetener ingredient is a natural sweetener. Optionally every sweetener ingredient is a steviol glycoside. Optionally every ingredient is an organic and/or natural ingredient, such that the reduced calorie (e.g., diet) carbonated cola beverage product is correspondingly an organic and/or natural beverage product.

Preferably, the consumable comprises at least one modified Rebaudioside A selected from those represented in FIG. 5.

For example, a beverage may comprise modified Rebaudioside A in concentrations of about 30 ppm—about 750 ppm (e.g. from about 50 ppm up to 350 ppm). However the amount added mainly depends on the level of sweetness desired and may depend on the presence of other ingredients. For example, fruit juice comprises sugar and thus contributes to the level of sweetness. In one embodiment, the modified Rebaudioside A is the only sweetener added to the flavored beverage. In another embodiment, modified Rebaudioside A may be combined with other sweetener and/or sweetness enhancers. In a preferred embodiment, the modified Rebaudioside A is combined with a mogroside, like mogroside V.

LEGENDS TO THE FIGURES

FIG. 1. Chemical structures of Stevioside, Rebaudioside A and B, and Steviolbioside. [G1c1], etc. denotation of glucose residues for NMR assignment.

Figure 2A:
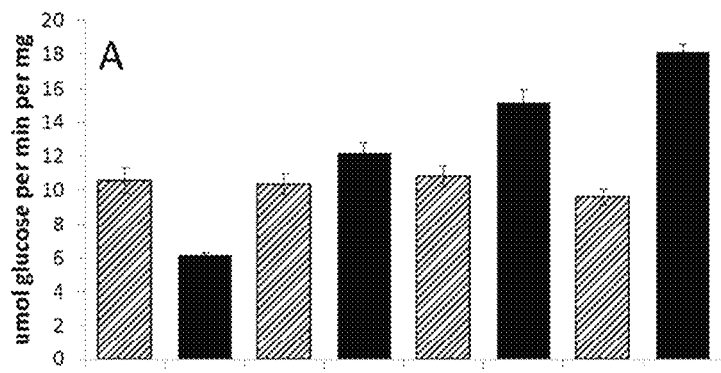
Figure 2B:
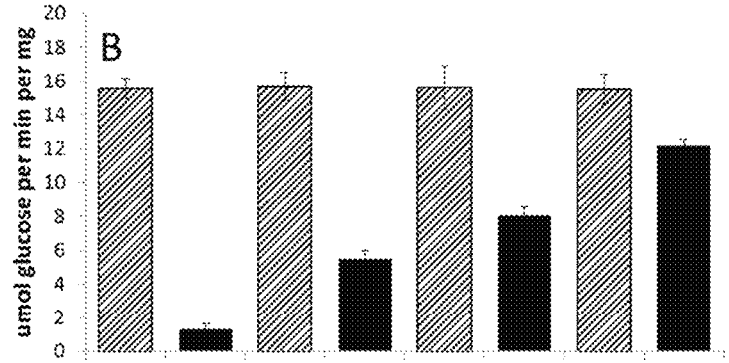
Figure 2C:
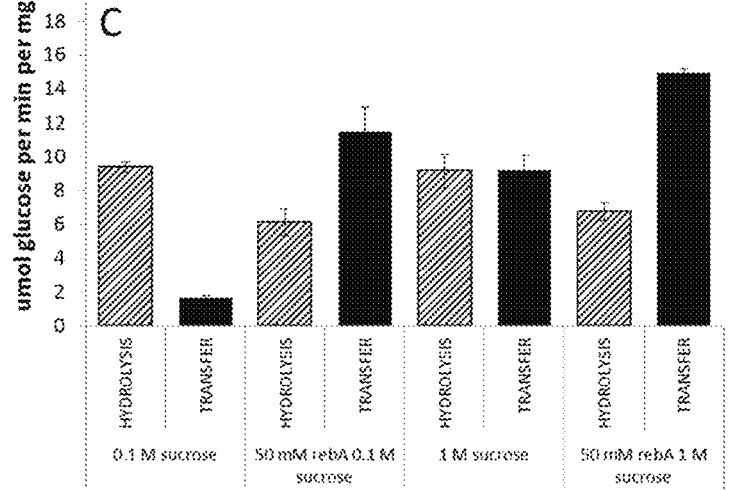

FIG. 2. Effect of Rebaudioside A and sucrose concentrations on the transglucosylation (solid bars) and hydrolysis (hatched bars) activity using 0.12 mg/mL purified enzyme: (A) GTF180-ΔN, (B) GTF180-ΔN mutant S1137Y and (C) GTF180-ΔN mutant Q1140E.

FIG. 3. NP-HPLC product profiles of a 4 hour incubation of 10 U/mL GTF180-ΔN(WT), mutant S1137Y and mutant Q1140E with 50 mM Rebaudioside A(*) and 1 M sucrose (**=RebAG1).

FIG. 4. Time course of Rebaudioside A utilization (dashed line) and RebAG1 formation by α-glucosylation (solid line) using 10 U/mL enzyme: (A) GTF180-ΔN, (B) GTF180-ΔN mutant S1137Y and (C) GTF180-ΔN mutant Q1140E, showing 55%, 73% and 96% conversion, respectively.

FIG. 5. Structures of modified Rebaudioside A glucosides produced by GTF180-ΔN and mutants GTF180-ΔN S1137Y and GTF180-ΔN Q1140E: (A) RebAG1=13-({β-D-glucopyranosyl-(1→2)-[β-D-glucopyranosyl-(1→3)-]β-D-glucopyranosyl}oxy)ent-kaur-16-en-19-oic acid α-D-glucopyranosyl-(1→6)-β-D-glucopyranosyl ester (B) 13-({β-D-glucopyranosyl-(1→2)-[β-D-glucopyranosyl-(1→3)-]β-D-glucopyranosyl}oxy)ent-kaur-16-en-19-oic acid α-D-glucopyranosyl-(1→6)-α-D-glucopyranosyl-(1→6)-β-D-glucopyranosyl ester (C) 13-({β-D-glucopyranosyl-(1→2)-[β-D-glucopyranosyl-(1→3)-]β-D-glucopyranosyl}oxy)ent-kaur-16-en-19-oic acid α-D-glucopyranosyl-(1→3)-α-D-glucopyranosyl-(1→6)-β-D-glucopyranosyl ester (D) The 500-MHz $^1$H NMR spectra of RebAG1 product of GTF180-ΔN (a) and mutants Q1140E (b) and S1137Y (c) recorded in D$_2$O at 334K.

Figure 6:
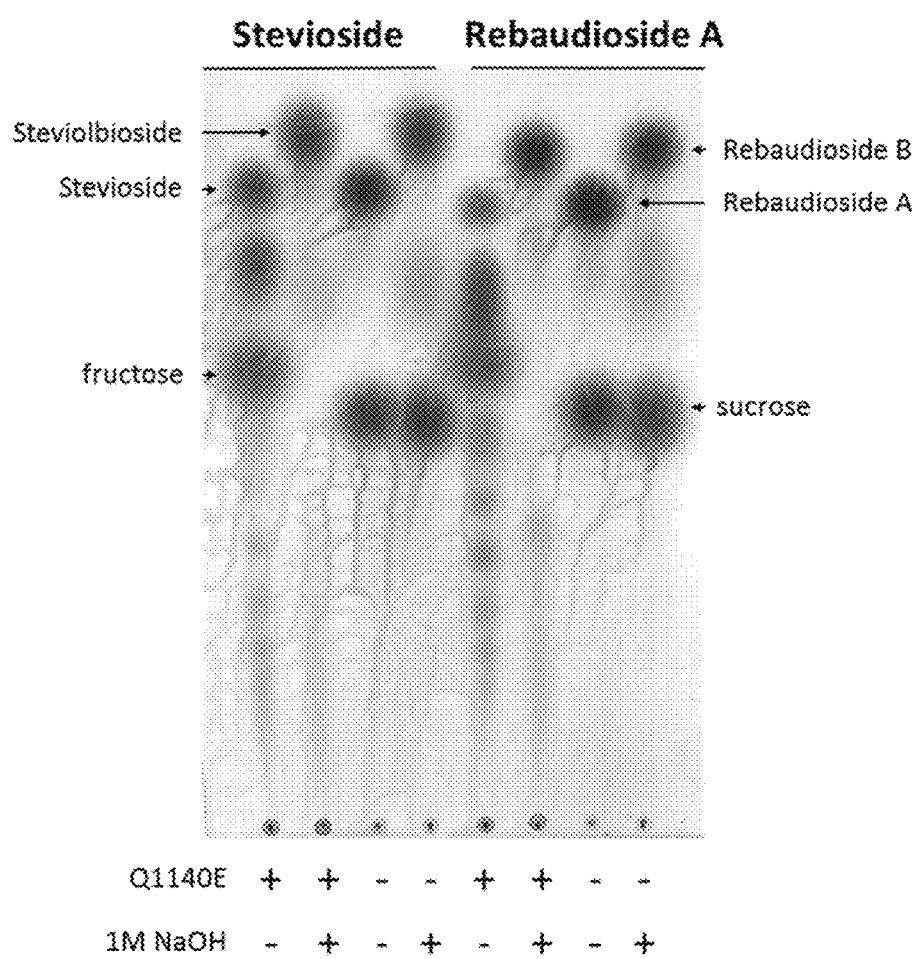

FIG. 6. TLC analysis of products obtained in a 1 hour incubation of 50 mM Stevioside and 50 mM Rebaudioside A with 100 mM sucrose with and without 20 U/ml Q1140E, before and after alkaline saponification with 1 M NaOH.

FIG. 7. Sensory evaluation (n=12) of several sweeteners: Stevioside (250 mg/L), Rebaudioside A (300 mg/L), RebAG1 (350 mg/mL), and sucrose (60 g/L). Evaluated taste attributes were sweetness (hatched bars) and bitterness (solid bars). Score 0=not sweet/not bitter, score 5=very sweet/very bitter.

Figure 8:
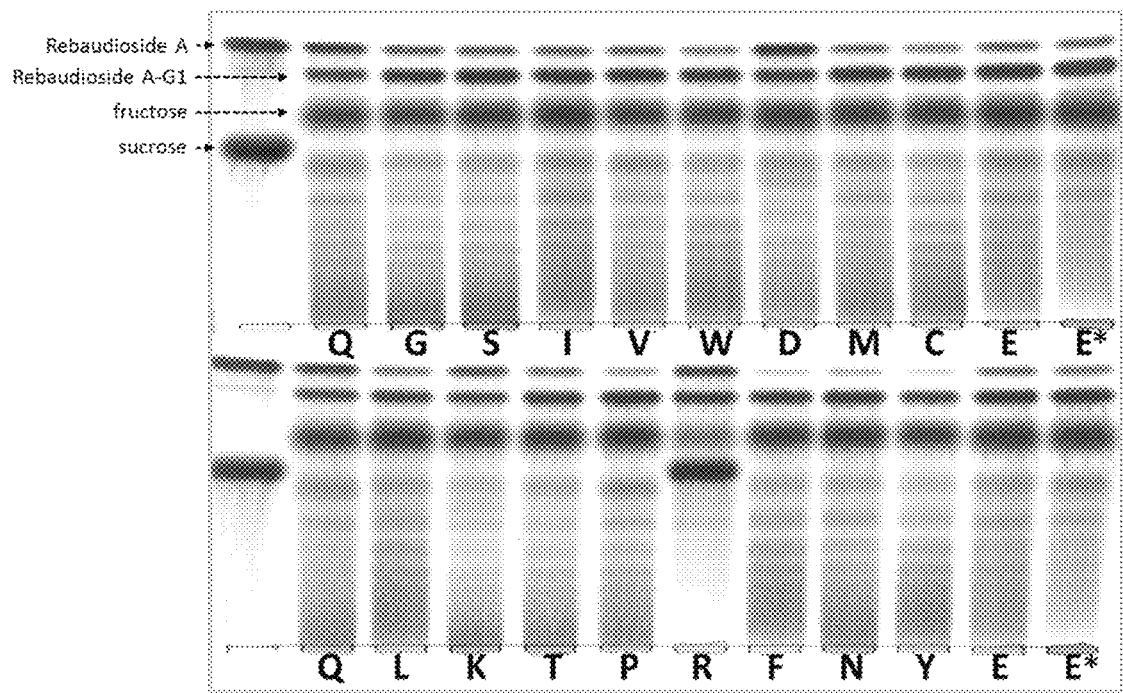

FIG. 8. TLC analysis of products obtained in a 2 hour incubation of 50 mM Rebaudioside A and 200 mM sucrose with GTF180-ΔNΔV (Q), GTF180-ΔNΔV Q1140 amino acid substitution mutants Q1140 G/S/I/V/W/D/M/C/E/L/K/T/P/R/F/N/Y, or GTF180-ΔN Q1140E (E*).

FIG. 9. Amino acid sequence of glucansucrase GTF180 from *Lactobacillus reuteri* 180. Panel (A) full length protein (SEQ ID NO:1); panel (B) N-terminally truncated mutant GTF180-ΔN (SEQ ID NO:2); panel (C) N-terminally truncated and domain V truncated mutant GTF180-ΔNΔV (SEQ ID NO:3).

EXPERIMENTAL SECTION

The section below exemplifies the advantageous use of glucansucrase GTF180-ΔN of *Lactobacillus reuteri* strain 180 and its derived single amino acid substitution mutants to α-glucosylate Rebaudioside A. GTF180-ΔN and derived mutant enzymes glucosylate Rebaudioside A specifically at the C-19 site, introducing (α1→6) and (α1→3) glycosidic linkages, which are resistant to hydrolysis by the amylolytic enzymes present in saliva. Several GTF180-ΔN mutants displayed a much higher transglucosylating activity towards Rebaudioside A than GTF180-ΔN. Interestingly, one mutant, Q1140E, showed nearly 100% conversion of Rebaudioside A and attached mostly a single (α1→6)-glucose at the C-19 site of Rebaudioside A.

The produced novel Rebaudioside A glucosides are very interesting, carrying one and two (α1→6)-linked glucose units specifically at the C-19 β-linked glucose. The mono-α-glucosylated Rebaudioside A product, RebAG1, has an increased and more natural sweetness and reduced bitterness compared to Rebaudioside A. These improved novel steviol glycosides of the invention are of great interest as functional food ingredients.

Materials and Methods

Steviol Glycoside Substrates

Rebaudioside A (2) and Stevioside (1) were purchased from Sigma Aldrich.

Glucansucrase Enzymes

All glucansucrase and fructansucrase enzymes were produced as described by Meng et al (2014) and purified as described by Kralj et al (2004b). GTF180-ΔN is the 117 kDa N-terminally truncated (741 residues) fragment of the GTF180 full-length protein (Kralj et al. 2004a). The construction of truncation mutant GTF180-ΔNΔV, consisting of amino acids 794-1636 of the GTF180 enzyme is described in Meng et al. (2015a).GTF180-ΔN mutant enzymes were created by van Leeuwen et al. (2009), Meng et al. (2015a), and Meng et al. (2015b). Amino acid substitutions in truncation mutant GTF180-ΔNΔV were created as described by Meng et al. (2015b)

Enzyme Activity Assays

Enzyme activity assays were performed at 100 mM and 1000 mM sucrose, with and without 50 mM Rebaudioside A in 25 mM sodium acetate (pH 4.7); 1 mM $CaCl_2$; and 0.12 mg/mL purified GTF180-ΔN enzyme or GTF180-ΔN mutant enzyme at 37° C. Samples of 100 µL were taken every 30 sec for 4 min and the reaction was immediately stopped by incubating with 20 µL 1000 mM NaOH for 30 min. The inactivated samples were diluted two times in deionized water and from 10 µL of the diluted sample the glucose and fructose concentrations were determined enzymatically by monitoring the reduction of NADP with the hexokinase and glucose-6-phosphate dehydrogenase/phosphoglucose isomerase assay (Roche) as described previously (Mayer 1987). Quantitative determination of the release of glucose and fructose from sucrose allowed estimation of the activities of the glucansucrase enzymes (van Geel-Schutten et al. 1999). Fructose release corresponds to the total enzyme activity and glucose release to the hydrolytic activity. The transglycosylation activity can be obtained by subtracting the hydrolytic activity from the total activity. One unit (U) of enzyme is defined as the amount of enzyme required for producing 1 µmol monosaccharide per min in a reaction mixture containing 25 mM sodium acetate (pH 4.7); 1 mM $CaCl_2$; and 1000 mM sucrose at 37° C.

Enzymatic Glycosylation of Steviol Glycosides

Incubation reactions were performed in 25 mM sodium acetate (pH 4.7), 1 mM $CaCl_2$, 50 to 1,000 mM sucrose, 50-100 mM steviol glycoside, and 2-30 U/mL purified GTF180-ΔN enzyme or GTF180-ΔN mutant enzyme at 37° C. for 15 min to 24 hours. Reactions were stopped by heat inactivation (100° C. for 15 min). From the inactivated samples 250 uL was mixed with 1000 ul of 10 mM catechol (internal standard) and subsequently purified by solid phase extraction using Strata-X 33u Polymeric Reversed Phase columns (Phenomenex). For HPLC analysis 20 µL of the purified sample was injected on a Luna 10 µm NH2 chromatography column (250 mm×4.6 mm; Phenomenex). Reaction components were separated at a flow-rate of 1 mL/min under gradient elution conditions, starting with a 2 min isocratic step of 70% solvent A followed by a linear gradient from 70 to 55% solvent A over 9 min (solvent A=acetonitrile; solvent B=0.025% acetic acid). Rebaudioside A and the mono-α-glucosylated Rebaudioside A product concentrations were determined with NP-HPLC, using their corresponding calibration curves ranging from 1.56 to 50 mM. All data were normalized with catechol as internal standard. The standard deviation of the response was less than 5%. All NP-HPLC analyses were performed on an UltiMate 3000 chromatography system (ThermoFischer Scientific, Amsterdam, The Netherlands), equipped with an Endurance autosampler (Spark Holland, The Netherlands).

Quantitative Synthesis of α-Glucosylated Rebaudioside A Products

For quantitative synthesis of α-glucosylated Rebaudioside A products using GTF180-ΔN and its derived mutants, incubations were performed in 5 mL 25 mM sodium acetate (pH 4.7), 1 mM $CaCl_2$, 50 mM steviol glycoside with two batches of 1,000 mM equivalent of sucrose donor (t=0 and 3 h) to a total of 2,000 mM sucrose, using 10 U/mL enzyme at 37° C. for 24 hours. Products were purified from the incubation mixture by solid phase extraction using Strata-X 33u Polymeric Reversed Phase columns (Phenomenex). Products were separated on a Luna 10 µm NH2 semi-preparative chromatography column (250 mm×10 mm, Phenomenex) and were manually collected at a flow-rate of 4.6 mL/min, starting with a 2 min isocratic step of 80% solvent A followed by a linear gradient of 80 to 50% solvent A over 38 min (solvent A=acetonitrile; solvent B=0.025% acetic acid). The solvent of the collected fractions was evaporated under a stream of nitrogen gas and the dried materials were dissolved in deionized water.

Thin-Layer Chromatography

Samples were spotted on TLC sheets (Merck Kieselgel 60 F254, 20×20 cm), which were developed with n-butanol: acetic acid:water=2:1:1. Spots were visualized by orcinol/sulfuric acid staining and compared with a simultaneous run of standard compounds.

Alkaline Saponification

To release the 19-O-linked glycosyl moiety, 4 mg of each steviol glycoside product was dissolved in 1 M NaOH (1 mL) and heated at 80° C. for 2.5 h.

Mass Spectrometry

Matrix-assisted laser desorption ionization time-of-flight mass spectrometry (MALDI-TOF-MS) experiments were performed using an Axima™ mass spectrometer (Shimadzu Kratos Inc., Manchester, UK) equipped with a Nitrogen laser (337 nm, 3 ns pulse width). Positive-ion mode spectra were recorded using the reflector mode at a resolution of 5000 FWHM and delayed extraction (450 ns). Accelerating voltage was 19 kV with a grid voltage of 75.2%. The mirror voltage ratio was 1.12 and the acquisition mass range was 200-6000 Da. Samples were prepared by mixing 1 µL sample solutions with 1 µL 10% 2,5-dihydroxybenzoic acid in 70% ACN as matrix solution.

NMR Spectroscopy

Resolution-enhanced 1D/2D 500-MHz $^1$H NMR spectra were recorded in $D_2O$ on a Bruker DRX-500 spectrometer (Bijvoet Center, Department of NMR Spectroscopy, Utrecht University) at a probe temperature of 334K. Data acquisition and processing were done with Bruker Topspin 2.1. Prior to analysis, samples were exchanged twice in $D_2O$ (99.9 atom % D, Cambridge Isotope Laboratories, Inc., Andover, Mass.) with intermediate lyophilization, and then dissolved in 0.6 mL D$_2$O. Suppression of the deuterated water signal (HOD at 4.40 ppm) was achieved by applying a WEFT (water eliminated Fourier transform) pulse sequence for 1D NMR experiments and by a pre-saturation of 1 s during the relaxation delay in 2D experiments. The 2D TOCSY spectra were recorded using an MLEV-17 (composite pulse devised by Levitt et al (1982)) mixing sequence with spin-lock times of 40-200 ms. The 2D ROESY spectra were recorded using standard Bruker XWINNMR software with mixing time of 200 ms. The carrier frequency was set at the downfield edge of the spectrum in order to minimize TOCSY transfer during spin-locking. Natural abundance 2D $^{13}$C-$^1$H HSQC experiments ($^1$H frequency 500.0821 MHz, $^{13}$C frequency 125.7552 MHz) were recorded without decoupling during acquisition of the $^1$H FID. Resolution enhancement of the spectra was performed by a Lorentzian-to-Gaussian transformation for 1D spectra or by multiplication with a squared-bell function phase shifted by $\pi/(2.3)$ for 2D spectra, and when necessary, a fifth order polynomial baseline correction was performed. Chemical shifts (δ) are expressed in ppm by reference to internal acetone (δ 2.225 for $^1$H and δ 31.07 for $^{13}$C).

Sensory Evaluation of Novel α-Glucosylated Products of Rebaudioside A

Taste evaluations were performed in which novel α-glucosylated products of Rebaudioside A (350 mg/L) were compared to sucrose (60 g/L), Rebaudioside A (300 mg/L), and stevioside (250 mg/L). In a blind test, twelve test persons that were able to perceive the bitter aftertaste of steviol glycosides were asked to rate sweetness and bitterness on a scale from 0 to 5, with 0 indicating not sweet/not bitter and 5 indicating very sweet/very bitter.

Results

Screening Glucan and Fructansucrase Enzymes for α-Glucosylation of Rebaudioside A Over a hundred glucan and fructansucrase wild type and mutant enzymes, mostly from *Lactobacillus reuteri*, were screened for Rebaudioside A α-glucosylation. For this, enzymes were incubated in 50 mM Rebaudioside A (FIG. 1) and 1000 mM sucrose for 3 hours. HPLC and TLC analysis of the reaction mixtures showed that only GTF180-ΔN enzyme and mutant enzymes of GTF180-ΔN were able to glucosylate Rebaudioside A (Table 1). Interestingly, two single GTF180-ΔN mutants S1137Y and Q1140E, which are single amino acid substitutions close to the transition state stabilizing residue D1136 (van Leeuwen et al. 2009) displayed much better transglucosylating activity towards Rebaudioside A than GTF180-ΔN. Also GTF180-ΔN mutants L981A and W1065L (Meng et al. 2015b) were able to α-glucosylate Rebaudioside A (Table 1), but showed almost no polymerization (i.e. oligosaccharide and glucan formation from sucrose) activity (data not shown). This is a clear advantage during downstream processing, the purification of the α-glucosylated Rebaudioside A products from mono- and disaccharides, oligosaccharides and glucans. By eliminating α-glucan synthesis, the most important side reaction, higher glycosylation yields were obtained for Rebaudioside A. At lower sucrose concentration (200 mM), these mutants had similar or even higher transglucosylating activity with Rebaudioside A than GTF180-ΔN and mutants S1137Y and Q1140E (data not shown).

TABLE 1

Overview of the Rebaudioside A α-glucosylation potential of glucansucrase and fructansucrase enzymes from various *Lactobacillus* strains.

| Enzyme | Mutation | *Glp (1→ | →3)Glp (→ | →4)Glp (→ | →6)Glp (→ | →3,6)Glp (→ | Activity on RebA |
|---|---|---|---|---|---|---|---|
| GTF180-ΔN[a] | N-terminal truncated GTF180[a] (**AY697430); Met-Gly-742-1772-His$_6$ | 12 | 24 | | 52 | 12 | + |
| GTF180-ΔNΔV[b] | domain V deletion mutant of GTF180-ΔN; Met-794-1636-His$_6$ | 12 | 23 | | 52 | 13 | + |
| GTF180-ΔN-PNNS[c] | triple amino acid mutant (V1027P: S1137N: A1139S) of GTF180-ΔN | 18 | 10 | 12 | 42 | 18 | + |
| GTF180-ΔN-SNAE[d] | single amino acid mutant (Q1140E) of GTF180-ΔN | 12 | 16 | 2 | 52 | 18 | ++++++ |
| GTF180-ΔN-SNAA[d] | single amino acid mutant (Q1140A) of GTF180-ΔN | 11 | 6 | | 69 | 14 | +/− |
| GTF180-ΔN-SNAH[d] | single amino acid mutant (Q1140H) of GTF180-ΔN | 8 | 8 | | 76 | 8 | +/− |
| GTF180-ΔN-NNA[d] | single amino acid mutant (S1137N) of GTF180-ΔN | 12 | 26 | 3 | 47 | 12 | ++ |
| GTF180-ΔN-YDA[d] | double amino acid mutant (S1137Y: N1138D) of GTF180-ΔN | 19 | 23 | 7 | 31 | 20 | ++++ |
| GTF180-ΔN-YNA[d] | single amino acid mutant (S1137Y) of GTF180-ΔN | 18 | 21 | 4 | 39 | 18 | ++++ |
| GTF180-ΔN-SDA[d] | single amino acid mutant (N1138D) of GTF180-ΔN | 10 | 24 | | 56 | 10 | + |
| GTF180-ΔN-XM1[e] | single amino acid mutant (L981A) of GTF180-ΔN | | | | | | ++ |
| GTF180-ΔN-XM2[e] | single amino acid mutant (W1065L) of GTF180-ΔN | | | | | | ++ |
| GTFA-ΔN[f] | N-terminal truncated GTFA (AX306822)[g] | 9 | | 46 | 34 | 12*** | −**** |
| GTFA-ΔN N1134S[h] | single amino acid mutant (N1134S) of GTFA-ΔN | 8 | | 12 | 76 | 4*** | − |
| GTFA-ΔN N1134E[h] | single amino acid mutant (N1134E) of GTFA-ΔN | 8 | | 49 | 36 | 7*** | − |
| GTFA-ΔN N1134A[h] | single amino acid mutant (N1134A) of GTFA-ΔN | 13 | | 25 | 49 | 13*** | − |

TABLE 1-continued

Overview of the Rebaudioside A α-glucosylation potential of glucansucrase and fructansucrase enzymes from various *Lactobacillus* strains.

| Enzyme | Mutation | *Glp (1→ | →3)Glp (→ | →4)Glp (→ | →6)Glp (→ | →3,6)Glp (→ | Activity on RebA |
|---|---|---|---|---|---|---|---|
| GTFA-ΔN NEV[h] | double amino acid mutant (N1135E: S1136V) of GTFA-ΔN | 10 | | 49 | 29 | 12*** | – |
| GTFB[a] | wild type (AY697435) | | | | | | – |
| GTFMLI[a] | N-terminal truncated GTFMLI (AY697431)[a] | | 47 | | 10 | 26*** | – |
| GTFO[i] | N-terminal truncated GTFO (AY911856)[i] | | | 67 | 13 | 15 | – |
| InuJ[j] | N-terminal truncated InuJ[j] fructansucrase | | | | | | – |
| InuGA-RM[k] | wild type fructansucrase | | | | | | – |
| InuGB-R[k] | wild type fructansucrase | | | | | | – |
| LevG-R[k] | wild type fructansucrase | | | | | | – |

[a]Kralj et al (2004a);
[b]Meng et al (2015);
[c]Van Leeuwen et al (2008);
[d]Van Leeuwen et al (2009);
[e]Meng et al. in prep.;
[f]Kralj et al (2004b);
[g]Kralj et al (2002);
[h]Kralj et al (2006);
[i]Kralj et al (2005);
[j]Anwar et al (2008);
[k]Anwar et al (2010);
*linkage distribution;
**Genbank accession number;
***→4,6)Glp (→;
****not active on Rebaudioside A (RebA)

To optimize the reaction conditions towards glucosylation of Rebaudioside A the effect of Rebaudioside A and sucrose on the transglucosylation activity of GTF180-ΔN and mutants S1137Y and Q1140E was determined. For this, enzyme activity assays were performed at 100 mM and 1000 mM sucrose with and without 50 mM Rebaudioside A. All three enzymes were more hydrolytic at low sucrose concentrations (FIG. 2). Both mutant enzymes were almost completely hydrolytic at 100 mM sucrose. However, when 50 mM Rebaudioside A was added to the reaction or when the sucrose concentration was increased to 1000 mM, the transglucosylation activity of all three enzymes was noticeably increased, showing the highest overall activity and highest transglucosylation to hydrolysis ratio at 1 M sucrose and 50 mM Rebaudioside A. These reaction conditions were used to follow the α-glucosylation of Rebaudioside A by GTF180-ΔN and mutants S1137Y and Q1140E in more detail.

When 50 mM Rebaudioside A, 1000 mM sucrose, and 10 U/mL enzyme was used, mutants S1137Y and Q1140E glucosylated respectively 73% and 96% Rebaudioside A compared to 55% by GTF180-ΔN (FIG. 4). To our surprise, mutant Q1140E mainly produced mono-glucosylated Rebaudioside A (RebAG1), yielding ~35 mM RebAG1 from 50 mM Rebaudioside A (FIG. 3 and FIG. 4). Mutant S1137Y produced a similar amount of RebAG1 as the GTF180-ΔN enzyme (~13 mM) (FIG. 3), but synthesized a higher amount of multiple glycosides (FIG. 3).

From all the tested glucan- and fructansucrase enzymes, mutant GTF180-ΔN Q1140E showed the highest Rebaudioside A glucosylation activity and displayed mainly mono-glucosylation of Rebaudioside A. Therefore, besides mutations Q1140 E/A/H also additional amino acid substitutions at position Q1140 were created in mutant GTF180-ΔNΔV and tested for Rebaudioside A glucosylation (FIG. 8). For this, 1 mg/ml of the enzymes was incubated for 2 hours at 37° C. with 50 mM Rebaudioside A and 200 mM sucrose in buffer (25 mM sodium acetate (pH 4.7), 1 mM CaCl$_2$). The incubation mixtures were analyzed by TLC (FIG. 8). Under these conditions, several Q1140 substitution mutants (for e.g. Q1140 F/N/Y) showed even a higher Rebaudioside A glucosylation than mutant Q1140E, although the latter one still had the highest mono-glucosylation yield. Some mutations (for e.g. Q1140D) had a slightly negative effect on Rebaudioside A glucosylation. Interestingly, mutant Q1140R showed almost no activity on sucrose, although Rebaudioside A glucosylation was hardly affected by the mutation. It appears that the sucrose was mainly used for glucosylation of Rebaudioside A and not for side reactions, such as oligosaccharide formation.

Isolation and Characterization of α-Glucosylated Products of Rebaudioside A Glucosides Produced by GTF180-ΔN and GTF180-ΔN Mutants S1137Y and Q1140E Looking at the molecular structure of Rebaudioside A (FIG. 1), there are four Glcp residues (Glc1, Glc2, Glc3 and Glc4) with a total of 14 free hydroxyl groups, which can act as acceptors for transglucosylation.

GTF180-Δconverts sucrose into oligo- and polysaccharides, catalyzing the transglucosylation of Glcp residues in (α1→3)- and (α1→6)-linkages (van Leeuwen et al. 2008), there are 3 potential (1→3) sites and 4 potential (1→6) sites present at Rebaudioside A for the first attachment of a Glc residue.

In order to isolate α-glucosylated products of Rebaudioside A glucosides for structural characterization, incubations were done with 10 U/mL enzyme with 50 mM Rebaudioside A and 1000 mM sucrose. After 3 hours 1000 mM extra sucrose was added to the reaction mixtures and incubated for an additional 21 hours. Glucosides were isolated from the reaction mixtures using semi-preparative NP-HPLC. Interestingly, NMR structural analysis and methylation analysis of the mono-α-glucosylated product showed that GTF180-ΔN and mutants S1137Y and Q1140E specifically and only glucosylated Rebaudioside A at the C-19 β-linked glucose, attaching an (α1→6)-linked glucose (100%), yielding RebAG1 (see also FIG. 5A).

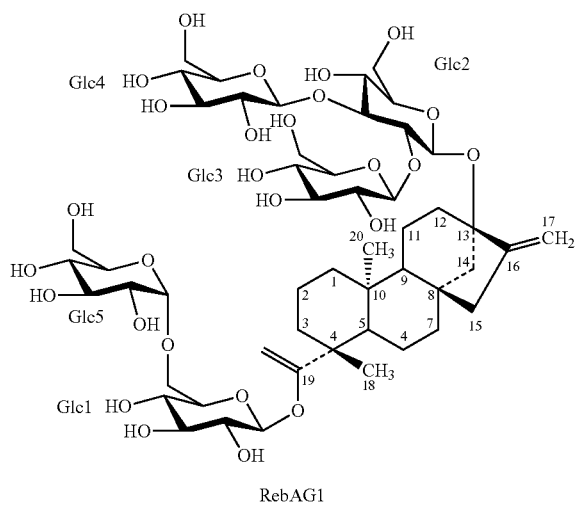

RebAG1

Figure 5D:
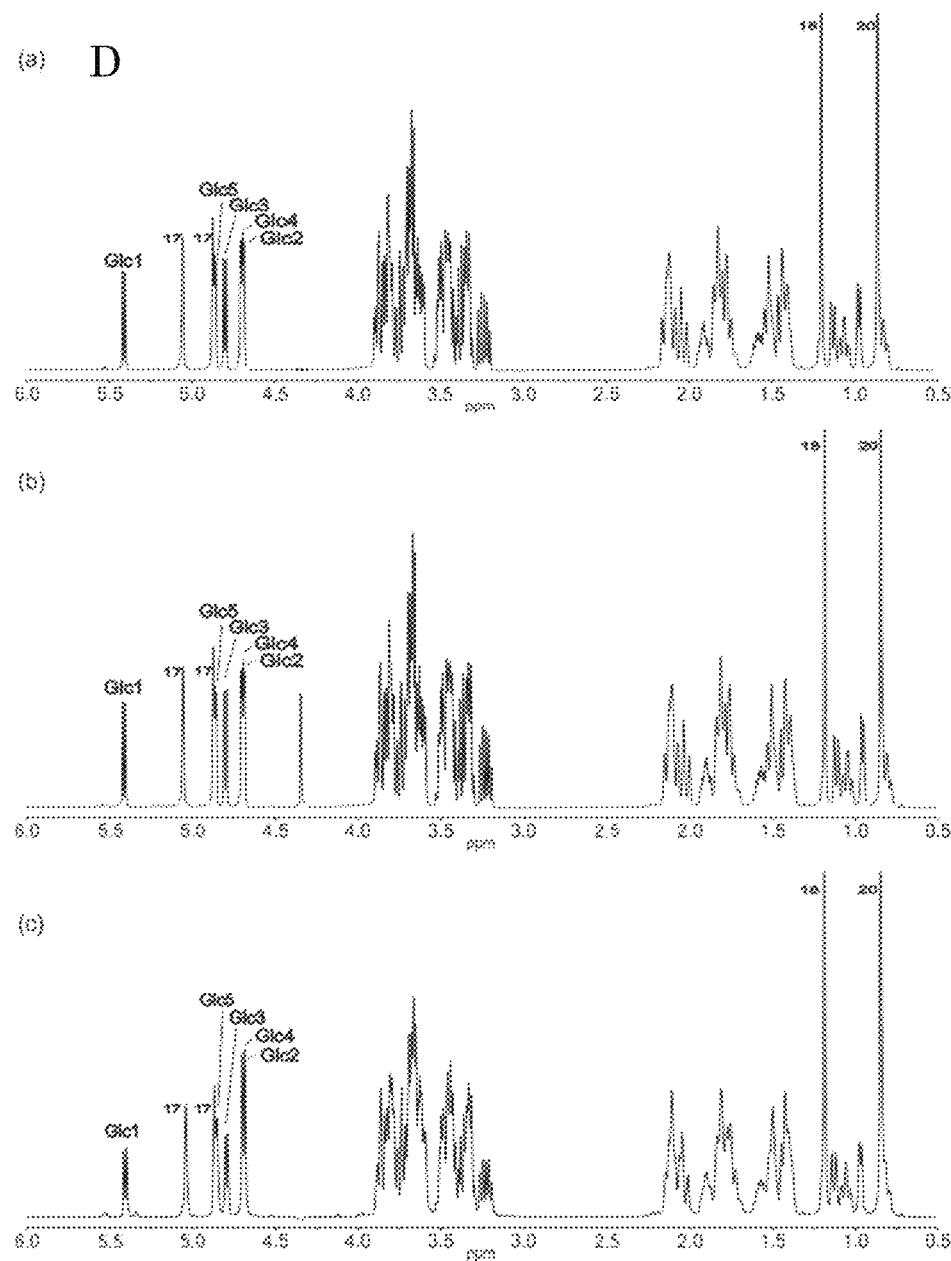

The di-glucosylated Rebaudioside A products of GTF180-ΔN and mutant S1137Y were both linear elongations of the structure of RebAG1 with an (α1→3)-linked glucose (~75%) (FIG. 5C) or another (α1→6)-linked glucose (~25%) (FIG. 5B). FIG. 5D panels (a), (b) and (c) show the 500-MHz 1H NMR spectra of RebAG1 produced by, respectively, GTF180-ΔN, GTF180-ΔN Q1140E and GTF180-ΔN S1137Y.

To confirm that introduction of extra Glcp residues via transglucosylation by GTF180-ΔN only occurred on the C-19 β-glucosyl moiety of Rebaudioside A, the isolated fractions were subjected to an alkaline saponification to specifically hydrolyze the 19-carboxyl-glucosyl ester bound (FIG. 1 and FIG. 6). Identical products were obtained from Rebaudioside A and the α-glucosylated products of Rebaudioside A, according to TLC, MALDI-TOF-MS (m/z 826 [M+H]$^+$) and NMR spectroscopy, being Rebaudioside A missing the complete glucosyl moiety at C-19. The resultant structure is known as Rebaudioside B (3) (FIG. 1).

C-19-Site Specific α-Glucosylation of Stevioside by GTF180-ΔN Mutant Q1140E

For commercial purposes it may be desirable to improve sweetness and decrease bitterness of the whole steviol glycoside leave extract. Since Stevioside (~5-10% w/w of dried leaves) is the most abundant and one of the most bitter tasting steviol glycosides, our aim was also to enhance the taste profile of Stevioside. Therefore, glucosylation reactions were also performed with GTF180-ΔN and substitution mutants derived thereof with Stevioside as the acceptor molecule. All three enzymes were also able to α-glucosylate stevioside. As observed with Rebaudioside A as acceptor molecule, mutant Q1140E converted Stevioside mainly into a single mono-α-glucosylated product (data not shown). In order to determine whether GTF180-ΔN mutant Q1140E glucosylates Stevioside also specifically at the C-19 site, steviol glucosides produced by Q1140E were subjected to alkaline saponification of the 19-carboxyl-glucosyl ester linkage with 1 M NaOH, to specifically remove the C-19 moiety. If alkaline saponification of the Q1140E steviol glucosides yields Steviolbioside (4)(FIG. 1) (i.e. Stevioside minus the C-19 moiety), then glucosylation occurred specifically at the C-19 site of Stevioside. On TLC plates multiple steviol glucosides were visible in the 1 hour incubation of Stevioside with Q1140E (FIG. 6). However, only one spot was observed when the incubation mixture was treated with 1 M NaOH and it migrated at the same height as the product formed after saponification of the Stevioside positive control. With MALDI-TOF analysis a molecular mass of 665.59 was detected, corresponding with the sodium-adduct of Steviolbioside. These results show that GTF180-ΔN Q1140E also specifically α-glucosylates Stevioside at the C-19 β-linked glucosyl moiety.

Taste Evaluation of the Newly Synthesized α-Glucosylated Products of Rebaudioside A To determine the effect of (α1→6) glucosylation at the 19-O-glucosyl moiety of Rebaudioside A on sweetness and bitterness, a taste evaluation was performed in which one the novel α-glucosylated products of Rebaudioside A, RebAG1, was compared to Rebaudioside A. For this, in a blind test, twelve test persons that were able to perceive the bitter aftertaste of steviol glycosides were asked to rate sweetness and bitterness on a scale from 0 to 5, with 0 indicating not sweet/not bitter and 5 indicating very sweet/very bitter. A clear trend was observed showing that the novel RebAG1 had an increased and a more natural sweetness and reduced bitterness compared to Rebaudioside A (FIG. 7).

REFERENCES

Brahmachari G, Mandal L C, Roy R, Mondal S, Brahmachari A K (2011) Stevioside and related compounds—molecules of pharmaceutical promise: a critical overview. Arch Pharm (Weinheim) 344:5-19. doi: 10.1002/ardp.201000181

Brandle J E, Starratt A N, Gijzen M (1998) *Stevia rebaudiana*: Its agricultural, biological, and chemical properties. Can J plant Sci 78:527-536.

Chatsudthipong V, Muanprasat C (2009) Stevioside and related compounds: therapeutic benefits beyond sweetness. Pharmacol Ther 121:41-54. doi: 10.1016/j.pharmthera.2008.09.007

Ciucanu I, Kerek F (1984) A simple and rapid method for the permethylation of carbohydrates. Carbohydr Polym 131: 209-217.

Darise M, Mizutani K, Kasai R, Tanaka O (1984) Enzymic transglucosylation of rubusoside and the structure-sweetness relationship of steviol-bisglycosides. Agric Biol Chem 10:2483-2488. doi: 10.1080/00021369.1984.10866520

DuBois G E, Dietrich P S, Lee J F, McGarraugh G V, Stephenson R A (1981) Diterpenoid sweeteners. Synthesis and sensory evaluation of stevioside analogues nondegradable to steviol. J Med Chem 24:1269-71.

DuBois G E, Stephenson R A (1985) Diterpenoid sweeteners. Synthesis and sensory evaluation of stevioside analogues with improved organoleptic properties. J Med Chem 28:93-8.

Fukunaga Y, Miyata T, Nakayasu N, Mizutani K, Kasai R, Tanaka O (1989) Enzymic transglucosylation products of stevioside: Separation and sweetness-evaluation. Agric Biol Chem 53:1603-1607. doi: 10.1271/bbb1961.53.1603

Geuns J (2003) Stevioside. Phytochemistry 64:913-921. doi: 10.1016/S0031-9422(03)00426-6

Goyal S K, Samsher, Goyal R K (2010) *Stevia (Stevia rebaudiana)* a bio-sweetener: a review. Int J Food Sci Nutr 61:1-10. doi: 10.3109/09637480903193049

Hellfritsch C, Brockho A, Sta F, Meyerhof W, Hofmann T (2012) Human psychometric and taste receptor responses to steviol glycosides. J Agric Food Chem 60:6782-6793.

Kamerling J P, Vliegenthart J F G (1989) Clinical Biochemistry—Principles, Methods, Applications. Walter de Gruyter, Berlin Kralj S, van Geel-Schutten G H, Dondorff M M G, Kirsanovs S, van der Maarel M J E C, Dijkhuizen L (2004a) Glucan synthesis in the genus *Lactobacillus*: isolation and characterization of glucansucrase genes, enzymes and glucan products from six different strains. Microbiol 150:3681-3690. doi: 10.1099/mic.0.27321-0

Kralj S, van Geel-Schutten G H, van der Maarel M J E C, Dijkhuizen L (2004b) Biochemical and molecular characterization of *Lactobacillus reuteri* 121 reuteransucrase. Microbiol 150:2099-2112. doi: 10.1099/mic.0.27105-0

Leemhuis H, Pijning T, Dobruchowska J M, van Leeuwen S S, Kralj S, Dijkstra B W, Dijkhuizen L (2013) Glucansucrases: three-dimensional structures, reactions, mechanism, α-glucan analysis and their implications in biotechnology and food applications. J Biotechnol 163:250-272. doi: 10.1016/j.jbiotec.2012.06.037

Lemus-Mondaca R, Vega-Gálvez A, Zura-Bravo L, Ah-Hen K (2012) *Stevia rebaudiana* Bertoni, source of a high-potency natural sweetener: A comprehensive review on the biochemical, nutritional and functional aspects. Food Chem 132:1121-1132. doi: 10.1016/j.foodchem.2011.11.140

Levitt M H, Freeman R, Frenkiel T (1982) Broadband Heteronuclear Decoupling. J Magn Reson 47:328-330.

Li S, Li W, Xiao Q, Xia Y (2013) Trans glycosylation of stevioside to improve the edulcorant quality by lower substitution using cornstarch hydrolyzate and CGTase. Food Chem 138:2064-9. doi: 10.1016/j.foodchem.2012.10.124

Lobov S V, Kasai R, Ohtani K, Yamasaki K (1991) Enzymic production of sweet stevioside derivatives: Transglucosylation by glucosidases. Agric Biol Chem 55:2959-2965.

Madan S, Ahmad S, Singh G N, Kohli K, Kumar Y, Singh R, Garg M (2010) *Stevia rebaudiana* (Bert.) Bertoni—A review. Indian J Nat Prod Resour 1:267-286.

Mayer R M (1987) Dextransucrase: a glucosyltransferase from *Streptococcus sanguis*. Methods Enzymol 138:649-661.

Meng X, Dobruchowska J M, Pijning T, Gerwig G J, Kamerling J P, Dijkhuizen L (2015a) Truncation of domain V of the multidomain glucansucrase GTF180 of *Lactobacillus reuteri* 180 heavily impairs its polysaccharide-synthesizing ability. Appl Microbiol Biotechnol 5885-5894. doi: 10.1007/s00253-014-6361-8

Meng X, Dobruchowska J M, Pijning T, López C A, Kamerling J P, Dijkhuizen L (2014) Residue Leu940 has a crucial role in the linkage and reaction specificity of the glucansucrase GTF180 of the probiotic bacterium *Lactobacillus reuteri* 180. J Biol Chem 289:32773-32782. doi: 10.1074/jbc.M114.602524

Meng X, Pijning T, Dobruchowska J M, Gerwig G J, Dijkhuizen L (2015b) Characterization of the functional roles of amino acid residues in acceptor binding subsite +1 in the active site of the glucansucrase GTF180 enzyme of *Lactobacillus reuteri* 180. J Biol Chem 290:30131-30141. doi: 10.1074/jbc.M115.687558

Musa A, Gasmalla M A A, Miao M, Zhang T, Aboshora W, Eibaid A, Jiang B (2014) Separation and structural characterization of tri-glucosyl-stevioside. J Acad Ind Res 2:593-598.

Prakash I, Markosyan A, Bunders C (2014) Development of Next Generation *Stevia* Sweetener: Rebaudioside M. Foods 3:162-175. doi: 10.3390/foods3010162

Puri M, Sharma D, Tiwari A K (2011) Downstream processing of stevioside and its potential applications. Biotechnol Adv 29:781-91. doi: 10.1016/j.biotechadv.2011.06.006

Shivanna N, Naika M, Khanum F, Kaul V K (2013) Antioxidant, anti-diabetic and renal protective properties of *Stevia rebaudiana*. J Diabetes Complications 27:103-13. doi: 10.1016/j.jdiacomp.2012.10.001 van Geel-Schutten G H, Faber E J, Smit E, Bonting K, Smith M R, Ten Brink B, Kamerling J P, Vliegenthart J F G, Dijkhuizen L (1999) Biochemical and structural characterization of the glucan and fructan exopolysaccharides synthesized by the *Lactobacillus reuteri* wild-type strain and by mutant strains. Appl Environ Microbiol 65:3008-3014.

van Leeuwen S S, Kralj S, Eeuwema W, Gerwig G J, Dijkhuizen L, Kamerling J P (2009) Structural characterization of bioengineered α-D-Glucans produced by mutant glucansucrase GTF180 enzymes of *Lactobacillus reuteri* strain 180. Biomacromolecules 10:580-588.

van Leeuwen S S, Kralj S, van Geel-Schutten I H, Gerwig G J, Dijkhuizen L, Kamerling J P (2008) Structural analysis of the alpha-D-glucan (EPS180) produced by the *Lactobacillus reuteri* strain 180 glucansucrase GTF180 enzyme. Carbohydr Res 343:1237-50. doi: 10.1016/j.carres.2008.01.042

Yadav S K, Guleria P (2012) Steviol glycosides from *Stevia*: biosynthesis pathway review and their application in foods and medicine. Crit Rev Food Sci Nutr 52:988-98. doi: 10.1080/10408398.2010.519447

Ye F, Yang R, Hua X, Shen Q, Zhao W, Zhang W (2013) Modification of stevioside using transglucosylation activity of *Bacillus amyloliquefaciens* α-amylase to reduce its bitter aftertaste. LWT—Food Sci Technol 51:524-530. doi: 10.1016/j.1wt.2012.12.005

The invention claimed is:

1. A method for enzymatically providing a modified steviol glycoside, comprising incubating a steviol glycoside substrate in the presence of sucrose as a glucose donor and a mutant of the glucansucrase GTF180 of *Lactobacillus reuteri* strain 180 comprising SEQ ID NO:1, SEQ ID NO:2 or SEQ ID NO:3, wherein said mutant GTF180 glucansucrase comprises one or more of the following amino acid substitutions: S1137Y, Q1140E, L981A, W1065L/E/Q/F, wherein SEQ ID NOs:1-3 represent the sequences of the full-length glucansucrase GTF180, the N-terminally truncated glucansucrase GTF180-ΔN, and the N-terminally truncated and domain V truncated glucansucrase GTF180-ΔNΔV, respectively, wherein S1137, Q1140, L981 and W1065 correspond to the amino acid positions of SEQ ID NO:1, wherein S1137 of SEQ ID NO:1 corresponds to S398 of SEQ ID NO: 2 and S345 of SEQ ID NO: 3, wherein Q1140 of SEQ ID NO:1 corresponds to Q401 of SEQ ID NO: 2 and Q348 of SEQ ID NO: 3, wherein L981 of SEQ ID NO:1 corresponds to L242 of SEQ ID NO: 2 and L189 of SEQ ID NO: 3, and wherein W1065 of SEQ ID NO:1 corresponds to W326 of SEQ ID NO: 2 and W273 of SEQ ID NO: 3.

2. The method according to claim 1, wherein said modified steviol glycoside is modified with at least one glucose residue.

3. The method according to claim 1, wherein said modified steviol glycoside is modified with one or more glucoses via an (α1→6) glycosidic bond, an (α1→3) glycosidic bond, or a combination thereof.

4. The method according to claim 1, wherein said modified steviol glycoside is modified at the C-13 and/or the C-19 site of the steviol glycoside.

5. The method according to claim 4, wherein said modified steviol glycoside is only modified at the C-19 site.

6. The method according to claim 5, wherein said modified steviol glycoside is only modified with a single glucose residue at the C-19 site.

7. The method according to claim 1, wherein said steviol glycoside substrate is a steviol glycoside.

8. The method according to claim 7, wherein said steviol glycoside is Rebaudioside A [13-({β-D-glucopyranosyl-(1→2)-[β-D-glucopyranosyl-(1→3)-]β-D-glucopyranosyl}oxy)ent-kaur-16-en-19-oic acid α-D-glucopyranosyl ester], or Stevioside (13-{[β-D-glucopyranosyl-(1→2)-β-D-glucopyranosyl]oxy}ent-kaur-16-en-19-oic acid α-D-glucopyranosyl ester).

9. The method according to claim 1 wherein said sucrose is added in a batchwise manner to a final amount of at least 1 M.

10. The method according to claim 1, wherein said mutant GTF180 glucansucrase is GTF180-ΔN Q401E, GTF180-ΔN Q401F, GTF180-ΔN Q401N, GTF180-ΔN Q401Y, GTF180-ΔN S398Y, GTF180-ΔN L242A, GTF180-ΔN W326L, GTF180-ΔN W326E, GTF180-ΔN W326Q and GTF180-ΔN W326F, GTF180-ΔNΔV Q348E, GTF180-ΔNΔV Q348F, GTF180-ΔNΔV Q348N, GTF180-ΔNΔV Q348Y, GTF180-ΔNΔV S345Y, GTF180-ΔNΔV L189A, GTF180-ΔNΔV W273L, GTF180-ΔNΔV W273E, GTF180-ΔNΔV W273Q and GTF180-ΔNΔV W273F.

* * * * *